US009956358B2

(12) United States Patent
Sias et al.

(10) Patent No.: US 9,956,358 B2
(45) Date of Patent: May 1, 2018

(54) INSUFFLATION STABILIZATION SYSTEM

(71) Applicant: Applied Medical Resources Corporation, Rancho Santa Margarita, CA (US)

(72) Inventors: Ralph Sias, Rancho Santa Margarita, CA (US); Alexandra Do, San Clemente, CA (US); Nikolai Poulsen, Rancho Santa Margarita, CA (US); Boun Pravong, Rancho Santa Margarita, CA (US); Kennii Pravongviengkham, Rancho Santa Margarita, CA (US); Timothy McMorrow, Rancho Santa Margarita, CA (US); W. F. Anthony Miles, East Preston (GB)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days. days.

(21) Appl. No.: 15/282,781

(22) Filed: Sep. 30, 2016

(65) Prior Publication Data
US 2017/0087311 A1  Mar. 30, 2017

Related U.S. Application Data

(60) Provisional application No. 62/235,128, filed on Sep. 30, 2015, provisional application No. 62/327,941, filed on Apr. 26, 2016.

(51) Int. Cl.
*A61B 17/34* (2006.01)
*A61M 13/00* (2006.01)
*A61B 17/00* (2006.01)

(52) U.S. Cl.
CPC ....... *A61M 13/003* (2013.01); *A61B 17/3423* (2013.01); *A61B 17/3474* (2013.01);
(Continued)

(58) Field of Classification Search
CPC ................ A61M 13/003; A61M 5/007; A61M 2202/0225; A61M 2202/00;
(Continued)

(56) References Cited

U.S. PATENT DOCUMENTS 3,858,572 A * 1/1975 Binard .................. A61M 5/007
600/560
4,207,887 A 6/1980 Hiltebrandt et al.
(Continued)

FOREIGN PATENT DOCUMENTS

EP  1 188 415 A2  3/2002
EP  1188415  *  3/2002  ......... A61B 17/3423
(Continued)

OTHER PUBLICATIONS

European Patent Office, The International Search Report and Written Opinion of the International Searching Authority for International Application No. PCT/US2016/054955 titled "Insufflation Stabilization System", dated Jan. 20, 2017, 21 pgs.

*Primary Examiner* — Pedro Philogene
(74) *Attorney, Agent, or Firm* — John F. Heal

(57) ABSTRACT

Pressure conditioning systems for supplying insufflation gas to an open-ended body conduit such as a rectal cavity during a transanal minimally invasive surgery (TAMIS) procedure can reduce billowing of walls of the body conduit. A pressure conditioning system can include a pressure storage component, an accumulator, and a flow restrictor. The pressure storage component can include a variable volume reservoir that is biased to a relatively low volume state. The flow restrictor can include insufflation tubing with a restric-
(Continued)

tor plate having a relatively low diameter orifice. The pressure storage component, accumulator, and flow restrictor can be fluidly connected in various orders in series or as side branches from a gas flow conduit. Despite a pulsed or otherwise discontinuous insufflation gas flow and leakage and absorption from the body conduit, the pressure conditioning system can maintain a constant pressure within the body conduit.

15 Claims, 24 Drawing Sheets

(52) U.S. Cl.
CPC ............ *A61B 2017/00278* (2013.01); *A61B 2017/00818* (2013.01); *A61B 2017/00862* (2013.01); *A61B 2017/3447* (2013.01); *A61M 2202/0225* (2013.01); *A61M 2205/3334* (2013.01); *A61M 2205/3341* (2013.01); *A61M 2205/3344* (2013.01); *A61M 2205/3355* (2013.01); *A61M 2210/1067* (2013.01)

(58) Field of Classification Search
CPC .. A61M 2205/3334; A61M 2205/3341; A61M 2205/3344; A61M 2205/33557; A61M 2210/1067; A61B 17/3423; A61B 17/3474; A61B 2017/00278; A61B 2017/00818; A61B 2017/00862; A61B 2017/3447
USPC ........ 600/200–205, 560; 604/23, 26, 65, 67, 604/132, 133, 140, 141, 151–153, 246, 604/890.1; 73/1.02
See application file for complete search history.

(56) References Cited

U.S. PATENT DOCUMENTS

| | | |
|---|---|---|
| 4,676,774 A | 6/1987 | Semm et al. |
| 4,966,578 A | 10/1990 | Baier et al. |
| 5,013,294 A | 5/1991 | Baier |
| 5,360,396 A | 11/1994 | Chan |
| 5,439,441 A | 8/1995 | Grimsley |
| 5,800,381 A | 9/1998 | Ognier |
| 6,217,555 B1* | 4/2001 | Hart ................ A61B 17/3462 128/DIG. 26 |
| 6,402,714 B1 | 6/2002 | Kraft-Kivikoski |
| 6,458,093 B1 | 10/2002 | Gord et al. |
| 7,285,112 B2* | 10/2007 | Stubbs ............... A61B 17/3421 128/898 |
| 8,157,763 B2 | 4/2012 | Williams, Jr. et al. |
| 8,366,667 B2 | 2/2013 | Chan et al. |
| 8,708,949 B2 | 4/2014 | Diemunsch et al. |
| 2007/0088275 A1 | 4/2007 | Stearns et al. |
| 2012/0310147 A1 | 12/2012 | Poll et al. |
| 2013/0245381 A1* | 9/2013 | Dang ................. A61B 17/0218 600/208 |
| 2014/0180198 A1* | 6/2014 | Ott ...................... A61M 13/003 604/24 |

FOREIGN PATENT DOCUMENTS

| | | |
|---|---|---|
| EP | 2 329 774 A1 | 6/2011 |
| WO | WO 2013/142150 A1 | 9/2013 |
| WO | WO 2014/077806 A1 | 5/2014 |

* cited by examiner

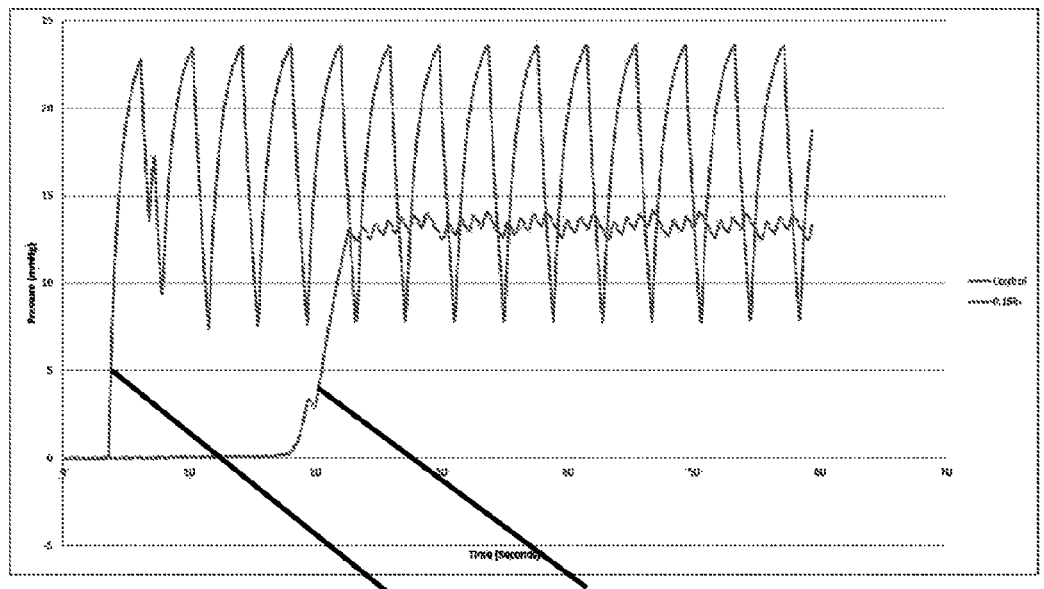
FIG. 28    980    992
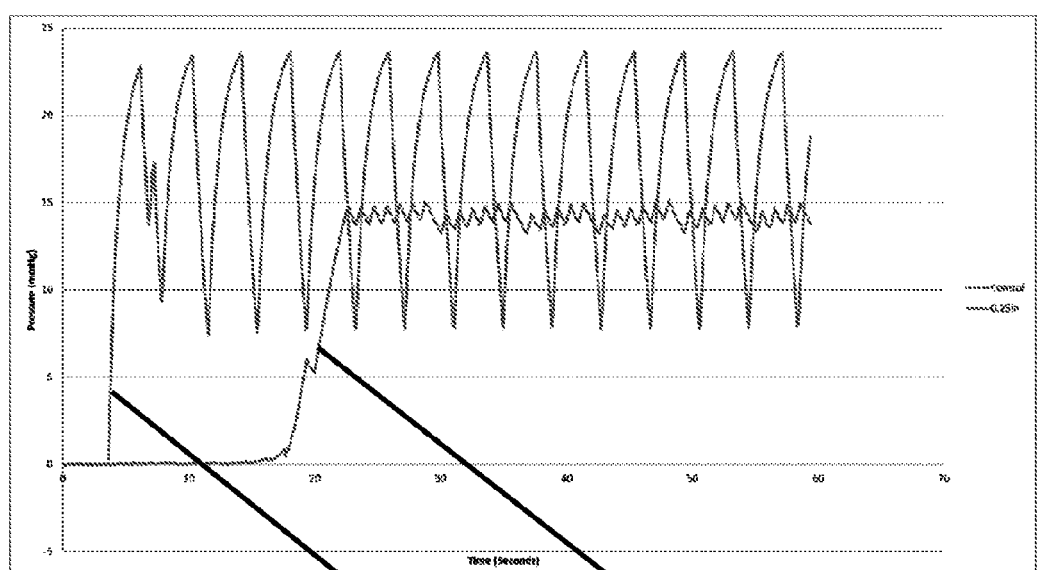
FIG. 29    980    994

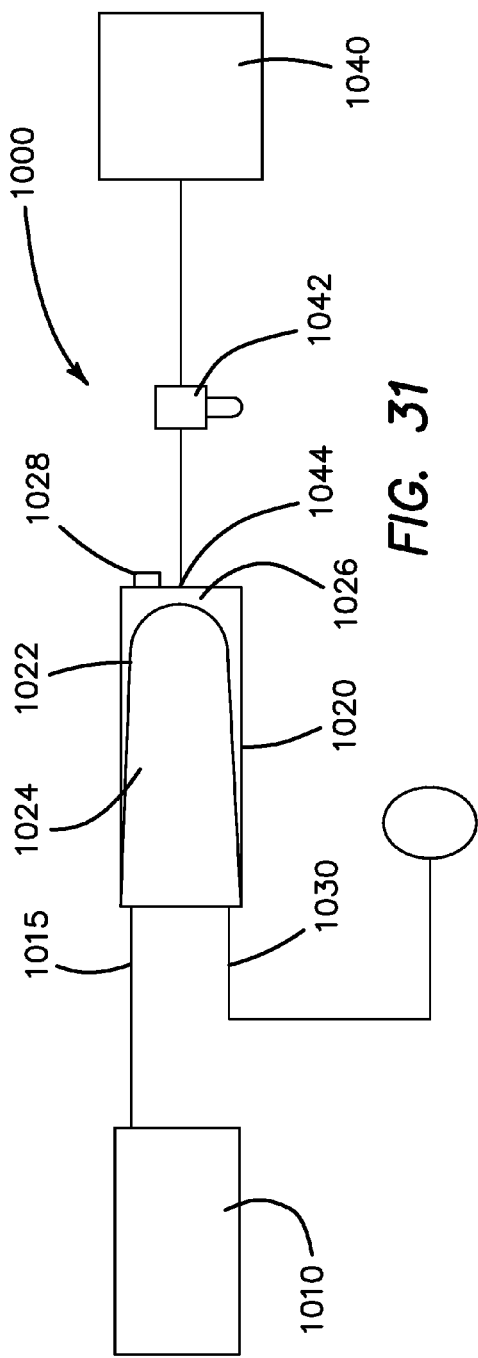
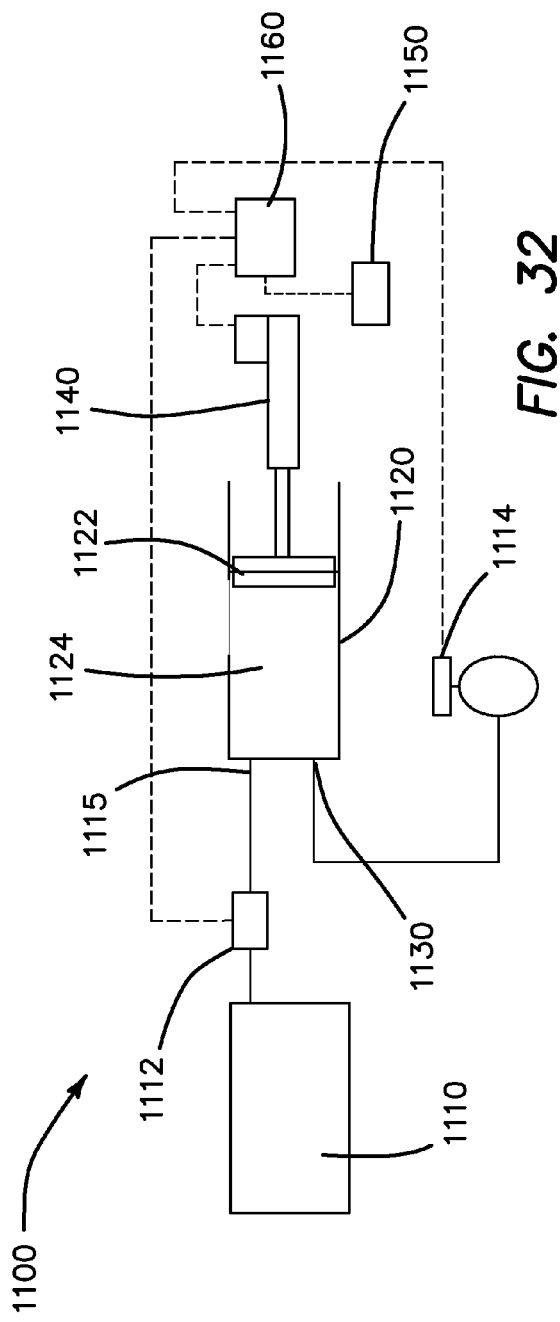

INSUFFLATION STABILIZATION SYSTEM

CROSS REFERENCE TO RELATED APPLICATIONS

This application claims the benefit of U.S. Provisional Patent Application Ser. No. 62/327,941, entitled "INSUFFLATION STABILIZATION SYSTEM," filed Apr. 26, 2016; and U.S. Provisional Patent Application Ser. No. 62/235,128, entitled "INSUFFLATION STABILIZATION SYSTEM," filed Sep. 30, 2015. The above-referenced applications are each incorporated by reference herein in their entireties.

BACKGROUND OF THE INVENTION

Field of the Invention

The present application relates to pressure conditioning apparatuses for surgical insufflation systems and more particularly to pressure conditioning apparatuses to maintain a substantially constant pressure at a surgical site despite pulsing or discontinuous insufflation supply and leakage and absorption at the surgical site.

Description of the Related Art

During Trans Anal Minimally Invasive Surgery (TAMIS) an insufflation machine is used to inflate the rectum with an insufflation gas such as carbon dioxide ($CO_2$). The inflation allows room for a surgeon to perform a surgical procedure using laparoscopic instruments and techniques. Many insufflation machines provide $CO_2$ in pulses, alternating pressurization pulses with pressure measurements. The colorectal system, however, is not a sealed volume and $CO_2$ continuously leaks from the inflated surgical area causing the pressure to drop. Additionally, $CO_2$ is readily absorbed by the walls of the colorectal system thereby exacerbating the loss of pressure caused by the leakage. $CO_2$ can leak from the system through a variety of leak paths, ranging from the length of the colorectal system, absorption by the intestine/colorectal walls, and through the surgical instruments and tools used to gain access. At some points of the procedure, a smoke evacuation port is constantly open in order to encourage the flow of $CO_2$, forcing out smoke generated by electrocautery. The multitude of leak paths leads to a loss of pressure and pulsed insufflation flow manifests itself as billowing of the rectal walls. The billowing follows the pressure cycle from the insufflation machine: when the machine is providing $CO_2$ pressure the rectal walls expand and when the insufflation machine is not supplying pressure (measuring the pressure) the rectal walls contract. The movement of the rectal walls can make laparoscopic surgery more difficult during a TAMIS, or other transanal procedure, which can require manipulation of and treatment of growths on the rectal walls.

SUMMARY OF THE INVENTION

In various embodiments, the apparatuses described herein can significantly reduce tissue billowing of an open-ended body conduit such as a rectal cavity that is insufflated by a pulsing insufflation pump. The apparatuses can condition a pulsed or discontinuous insufflation gas flow to provide a substantially continuous insufflation gas flow that can have a flow rate that varies responsive to pressure losses at an inlet from a zero pressure differential state between pulses of an insufflation pump and backpressure reduction at an outlet due to leakage and absorption by tissue at a surgical site in an open-ended body conduit. Moreover, the apparatuses can absorb energy from a relatively high flow output from an insufflator and provide a lower, but more continuous flow to the surgical field.

In certain embodiments, a gas flow pressure conditioning apparatus for use with a pulsing insufflation pump is provided. The apparatus comprises an inlet fluid port, an outlet fluid conduit, and a reservoir. The inlet fluid port is configured to receive a flow of gas from the pulsing insufflation pump. The outlet fluid conduit is configured to provide a flow of insufflation gas to a surgical site. The reservoir is fluidly coupled to the inlet fluid conduit and the outlet fluid conduit. The inlet fluid port has a first inner diameter and the outlet fluid conduit has a second inner diameter larger than the first inner diameter.

In certain embodiments, an insufflation system is provided. The insufflation system comprises a surgical access port and a gas flow pressure conditioning apparatus for use with a pulsing insufflation pump. The surgical site access port comprises a port surface, a first trocar, and a second trocar. The first trocar is positionable through the port surface. The first trocar has a first instrument channel extending therethrough. The second trocar is positionable through the port surface. The second trocar has a second instrument channel extending therethrough and an insufflation port. The gas flow pressure conditioning apparatus comprises an inlet fluid conduit, an outlet fluid conduit, and a reservoir. The inlet fluid conduit is configured to receive a flow of gas from the pulsing insufflation pump. The outlet fluid conduit is configured to provide a flow of insufflation gas to the surgical site access port. The reservoir is fluidly coupled to the inlet fluid conduit and the outlet fluid conduit. The inlet fluid conduit has a first inner diameter and the outlet fluid conduit has a second inner diameter larger than the first inner diameter.

In certain embodiments, a gas flow pressure conditioning apparatus for use with a pulsing insufflation pump is provided herein. The apparatus comprises an inlet port, an accumulator, a pressure storage vessel, and an outlet port. The inlet port is configured to receive a flow of gas from the pulsing insufflation pump. The accumulator fluidly is coupled to the inlet port. The pressure storage vessel is fluidly coupled to the inlet port. The flow restrictor is fluidly coupled to the inlet port. The outlet port is fluidly coupled to the inlet port and disposed downstream of the accumulator, the pressure storage vessel, and the flow restrictor.

In certain embodiments, an insufflation system for maintaining substantially constant pressure at a surgical site is provided herein. The insufflation system comprises a pulsing insufflation pump, and a pressure conditioning apparatus. The insufflation pump has a pump outlet. The pressure conditioning apparatus comprises an inlet, a pressure storage container, a reservoir, a flow restrictor, and an outlet port.

In certain embodiments, a surgical site sealing apparatus for sealing an open ended body conduit is provided herein. The sealing apparatus comprises an elastomeric bag. The elastomeric bag has an open end and a closed end opposite the open end. The elastomeric bag is sized and configured to be positioned within a body conduit. The elastomeric bag has an insertion configuration in which the bag is advanceable within the body conduit in an undisturbed state. The elastomeric bag is inflatable to an insufflated condition in which the elastomeric bag distends the body conduit.

In certain embodiments, a surgical site sealing apparatus for sealing an open ended body conduit is provided herein. The sealing apparatus comprises an inflatable member and an inflation tube. The inflatable member has a deflated state sized to be advanced through an open end of the body conduit. The inflatable member is inflatable by fluid to an inflated state sized to sealingly engage with walls of the body conduit. The inflation tube extends from a proximal end to a distal end and having a lumen extending between the proximal end and the distal end, the distal end of the inflation tube coupled to the inflatable member, and the lumen fluidly coupled to the inflatable member to provide the fluid to the inflatable member.

In certain embodiments, a surgical site sealing apparatus for sealing an open ended body conduit is provided herein. The sealing apparatus comprises a diaphragm and a flexible ring. The flexible ring disposed around the diaphragm, the flexible ring configurable in a first configuration in which the flexible ring is advanceable through the body conduit and a second configuration in which the flexible ring is sealingly engageable with a wall of the body conduit.

In certain embodiments, an insufflation system for maintaining substantially constant pressure at a surgical site is provided. The insufflation system comprises a reservoir. The reservoir comprises an insufflation chamber, a pressurization chamber, and a separation member. The insufflation chamber comprises an inlet port fluidly couplable to an insufflation pump and an outlet port. The pressurization chamber comprises a pressurization port couplable to a source of pressurized fluid and a pressure relief valve. The separation member fluidly isolates the insufflation chamber from the pressurization chamber. The separation member is movable responsive to an insufflation pressure in the insufflation chamber and a pressurization pressure in the pressurization chamber.

In certain embodiments, an insufflation system for maintaining substantially constant pressure at a surgical site is provided. The insufflation system comprises a reservoir and a pressure control system. The reservoir comprises an insufflation chamber and a piston. The insufflation chamber comprises an inlet port fluidly couplable to an insufflation pump and an outlet port. The piston is slidable within the reservoir to define a volume of the insufflation chamber. The pressure control system comprises a flow sensor fluidly coupled to the inlet port, a pressure sensor fluidly coupled to the outlet port, a linear actuator, and a programmable logic controller. The linear actuator is operably coupled to the piston. The linear actuator has a position feedback sensor. The programmable logic controller is electrically coupled to the flow sensor, the pressure sensor, the linear actuator, and the position feedback sensor. The logic controller is configured to actuate the linear actuator to position the piston in a position within the reservoir to maintain a desired pressure at the outlet port responsive to electrical signals from the flow sensor and the pressure sensor.

BRIEF DESCRIPTION OF THE DRAWINGS

FIG. 28 is a graph of surgical site pressure over time for a simulated surgical access site insufflated with a pulsatile insufflation pump and another embodiment of pressure conditioning apparatus;

FIG. 29 is a graph of surgical site pressure over time for a simulated surgical access site insufflated with a pulsatile insufflation pump and another embodiment of pressure conditioning apparatus;

FIG. 31 is a schematic view of an embodiment of insufflation system;

FIG. 32 is a schematic view of another embodiment of insufflation system;

DETAILED DESCRIPTION OF THE INVENTION

In various embodiments, a gas insufflation pressure conditioning apparatus can be fluidly coupled to a pulsing insufflation machine to alleviate billowing of a body conduit and reduce or eliminate the movement of the rectum walls when using the pulsing insufflation machine in a TAMIS procedure. The pressure conditioning apparatus can be configured to maintain a substantially constant pressure and flow in the body conduit despite leakage and absorption from the body conduit at the surgical site and a pulsing insufflation gas flow profile. Additionally, billowing can be further alleviated through provision of a body conduit sealing or closure device to create a closed volume within the rectal cavity to minimize the pressure lost while eliminating the movement of the rectum walls.

With reference to FIGS. 1-4 an embodiment of insufflation gas pressure conditioning apparatus 70 is illustrated. In the illustrated embodiment, the pressure conditioning apparatus 70 comprises a gas flow path extending from a segment of inlet gas tubing 92 through an elastomeric film pouch to a segment of outlet gas tubing 94. Advantageously, the elastomeric film pouch provides pressure conditioning functions of pressure storage, insufflation gas volume accumulation, and flow restriction to maintain a substantially consistent insufflation gas flow at a surgical site despite a discontinuous, pulsatile flow from an insufflator.

Figure 1:
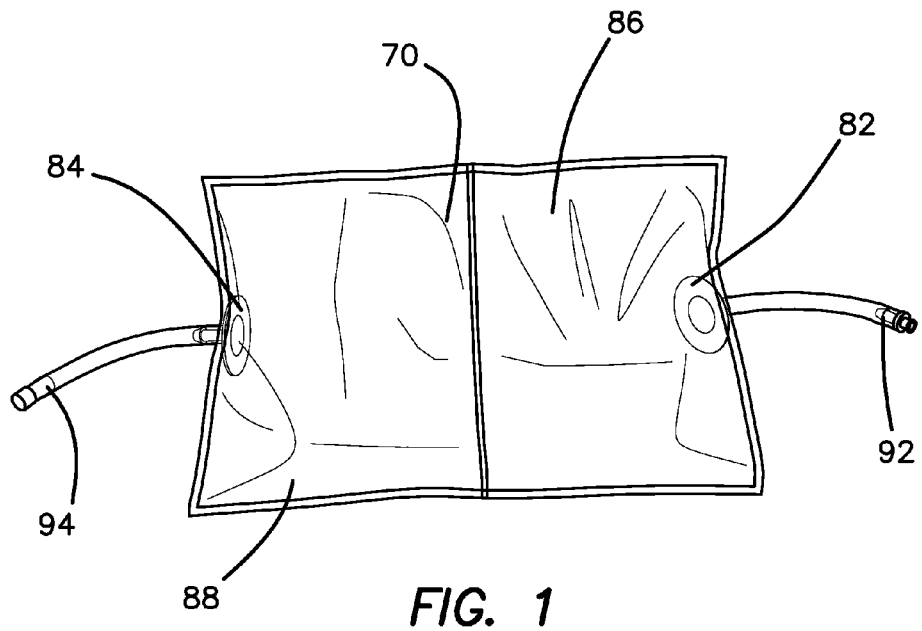
FIG. 1 is a side view of an embodiment of gas flow pressure conditioning apparatus.

With reference to FIG. 1, the film pouch 86 can be formed of a sheet of polymeric film that is folded upon itself and welded to seal edges 88 and create an enclosed volume. In the illustrated embodiment, with the pouch 86 in a deflated condition, the pouch has a generally rectangular shape with relatively long width and a relatively shorter height. It is contemplated that in other embodiments, the pouch can be formed in other shapes to achieve desired product packaging, aesthetic, or gas flow considerations.

With continued reference to FIG. 1, an inlet port 82 and an outlet port 84 can be added to the film pouch 86 to create a gas flow path through the pouch. In the illustrated embodiment, the inlet port 82 and outlet port 84 are positioned on opposite sides of the pouch 86 to provide a relatively direct flow path along a longitudinal axis of the width of the pouch 86. In other embodiments, it is contemplated that other positions of the inlet port 84 and outlet port 86 can be used to vary the gas flow characteristics of the pressure conditioning apparatus. For example, in some embodiments, the inlet port 82 and outlet port 84 can be positioned adjacent one another along one edge or can be positioned on opposite edges with respect to the height of the pouch 86 such that the pressure conditioning apparatus can have attributes of a side branch attenuator (schematically illustrated in FIG. 18C).

In the illustrated embodiment, the inlet port 82 and outlet port 84 can each comprise a bag port having a barbed fitting, such as are commercially available from Value Plastics, Inc. The pressure conditioning apparatus can further comprise a segment of inlet tubing 92 coupled to the barbed fitting of the inlet port 82 and a segment of outlet tubing 94 coupled to the barbed fitting of the outlet port 84. In some embodiments, the outlet port 84 can be coupled directly to insufflation tubing. In other embodiments, the outlet port 84 and outlet tubing 94 can be formed as a single component. The inlet tubing 92 can have a fitting end configured to be coupled to an insufflator or to insufflation tubing from an insufflator. The outlet tubing 94 can have a fitting end configured to be coupled to insufflation tubing fluidly coupled to a surgical access port.

While the illustrated embodiment includes both an inlet tubing 92 and an outlet tubing 94, in certain embodiments, it can be desirable that the pressure conditioning apparatus can include only a single length of tubing, or can be provided solely with ports. For example, in certain embodiments, a pressure conditioning apparatus can include an inlet port 82 at an upstream end and an outlet tubing 94 at a downstream end. Thus a desired length of inlet tubing can be associated with an insufflator. In other embodiments, a pressure conditioning apparatus can include an inlet port 82 at an upstream end and an outlet port 84 at a downstream end such that inlet and outlet tubing can be associated with an insufflator and a surgical access port. Moreover, in some embodiments, one or both of the inlet and outlet ports can include a luer fitting rather than a barbed fitting such that at least one of the inlet port and the outlet port comprises a luer port. In some embodiments, at least one of the inlet port and the outlet port can be heat sealed to the pouch. FIG. 3A illustrates an embodiment of pressure conditioning apparatus 70 having a film pouch 86 with an inlet port 82' having a luer fitting, and an outlet port 84' coupled to a length of outlet tubing 94' that is coupled to an insufflation trocar 940. In the illustrated embodiment, the outlet tubing 94' is a segment of corrugated tubing, which can be desirable in insufflation systems to reduce kinking of the tubing and the potential for related fluid flow disruptions.

The pouch 86 can be sized and configured to provide pressure conditioning aspects of a separate pressure storage component and accumulator of other embodiments of pressure conditioning devices herein. For example, in some embodiments, the pouch can be formed of a polymeric material having predetermined thickness and elasticity properties to provide the desired pressure storage. In some embodiments, the pouch 86 can be formed of a polyurethane film that can expand and contract responsive to insufflation pressure. It is contemplated that in other embodiments, other film materials and/or thicknesses can be used in a pressure conditioning apparatus to achieve the desired pressure storage.

The pouch 86 can be sized to stabilize the volume of an open-ended body conduit at a surgical site location supplied with pulsed insufflation. As further described with respect to FIGS. 2, 3, and 20-30, in some embodiments, a pouch 86 can be sized to provide a desired pressure conditioning profile for a TAMIS procedure. Desirably, in certain embodiments, the pouch 86 can have a volume of at least approximately 6.5 liters. In other embodiments, the pouch 86 can have a volume of between approximately 6.5 and approximately 8 liters. In one embodiment, the pouch 86 can have a volume of approximately 7.4 liters. Where the pouch has a pouch volume that is undesirably small for the surgical site, there can be insufficient pressure storage and accumulated volume to condition pulse cycles of an insufflation pump. Where the pouch is undesirably large for the surgical site, there can be an insufflation lag time as pulse cycles of the insufflator can be influenced by pressure fluctuations of the relatively large pouch volume rather than the surgical site. It is contemplated that the pouch can be configured with a different pouch volume than the range discussed above for use in patients having particularly small or particularly large colorectal volume. Likewise, it is contemplated that the pouch can have a different pouch volume if it is desired to use the pressure conditioning apparatus 70 to condition insufflation pressure pulses at a different surgical site.

Figure 2:
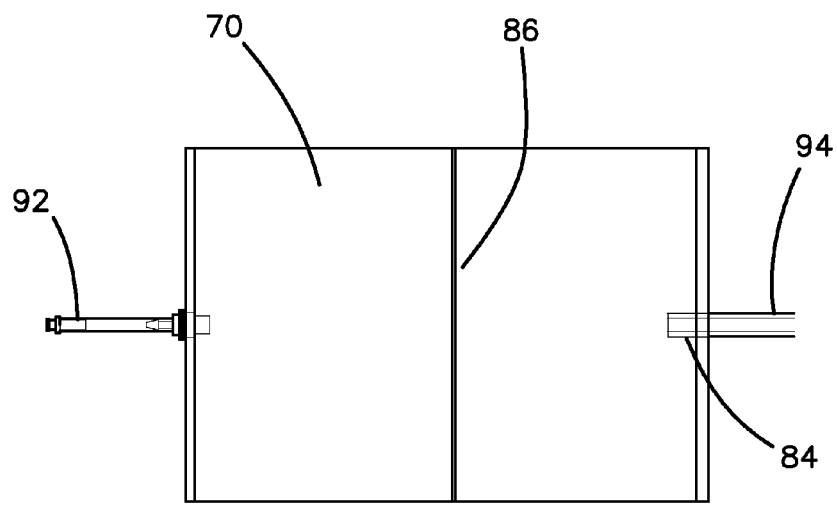
FIG. 2 is a schematic view of the embodiment of pressure conditioning apparatus of FIG. 1 for use in a surgical site access system.

With reference to FIG. 2, the pressure conditioning apparatus of FIG. 1 is schematically illustrated. The pressure conditioning apparatus 70 comprises an elastomeric film pouch 86 or bag that can have an inlet port 82 and an outlet port 84 that create a gas flow path through the pouch. The pressure conditioning apparatus can further comprise an inlet fluid conduit such as a length of inlet gas tubing 92 and an outlet fluid conduit such as a length of outlet gas tubing 94. The inlet gas tubing 92 can include a fitting or coupling to be fluidly coupled to an insufflation pump.

With continued reference to FIG. 2, in some embodiments the inlet gas tubing 92 and outlet gas tubing 94 can be sized relative to one another to provide a desired pressure conditioning profile. For example, in the illustrated embodiments, the inlet tubing 92 can have a first inner diameter and the outlet tubing 94 can have a second inner diameter larger than the first inner diameter.

Figure 3:
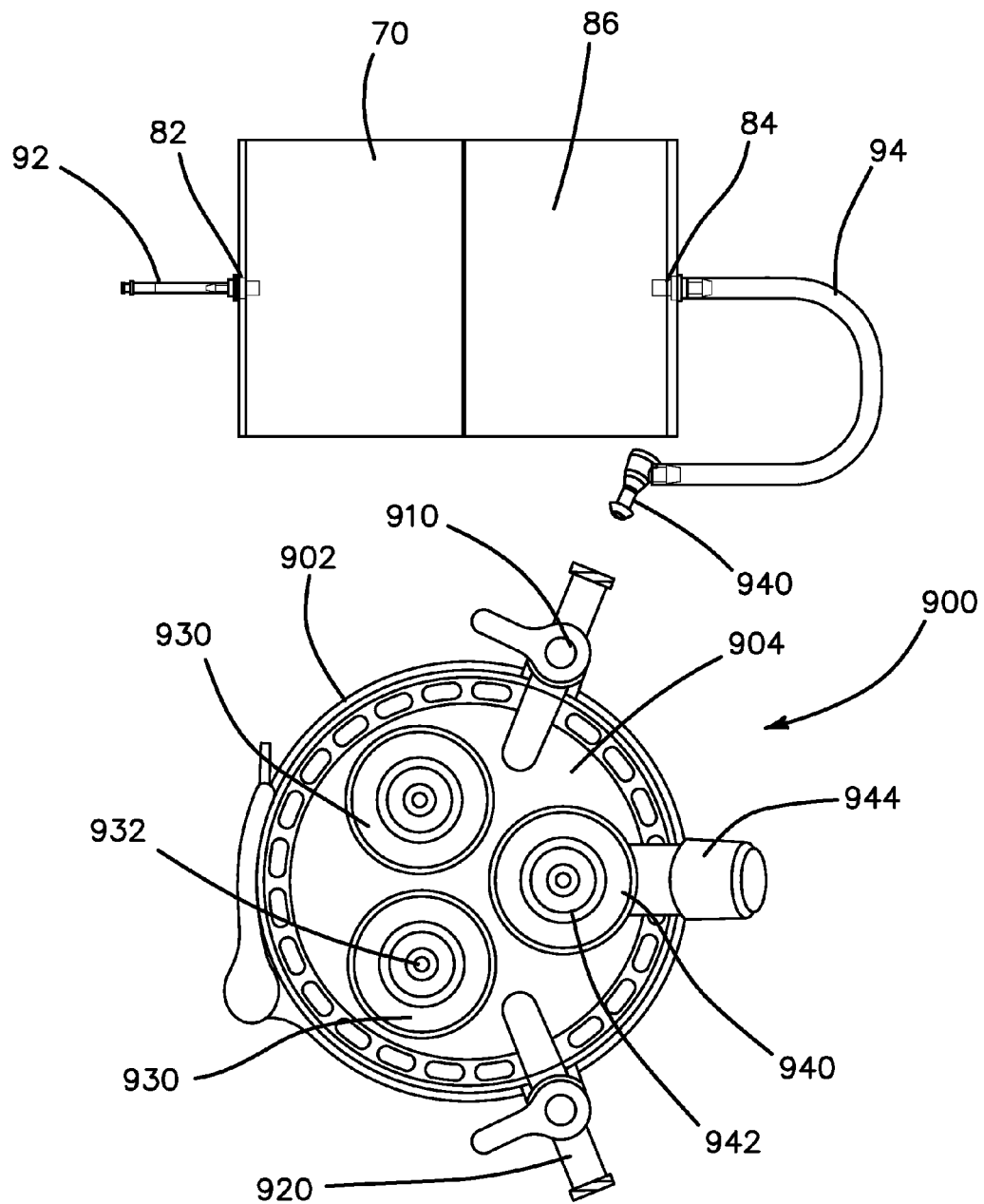
FIG. 3 is a schematic view of an embodiment of surgical site access system including the pressure conditioning apparatus of FIG. 1.
Figure 3A:
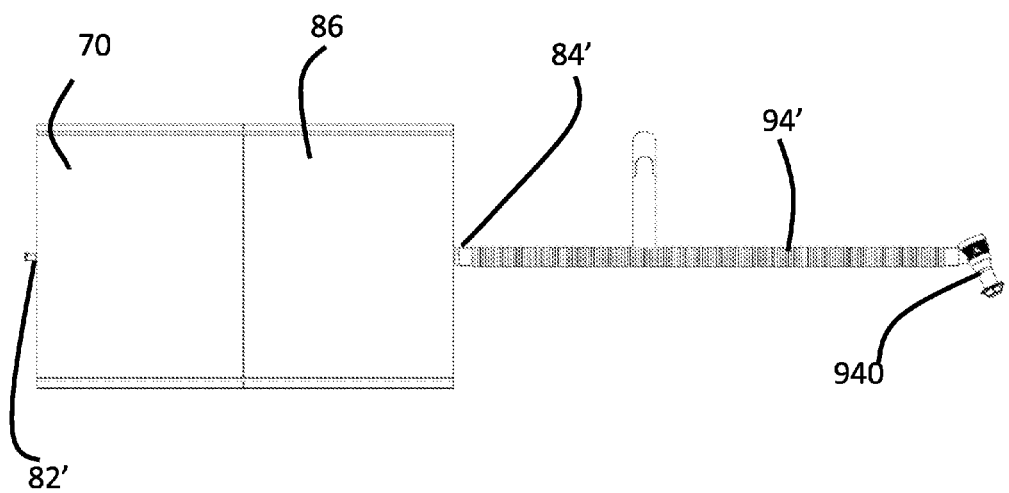
FIG. 3A is a schematic view of another embodiment of pressure conditioning apparatus for a surgical site access system.

With reference to FIGS. 2-3 in some embodiments, a pressure conditioning apparatus 70 as described herein can be included in a surgical site access system 900 such as a surgical access port 902 having a port surface 904 such as an artificial body wall defined by a gel surface of a surgical access port sold under the trademarks GELPORT and GELPOINT. In certain embodiments, the pressure conditioning apparatus 70 as described herein can be included in a surgical site access system configured for application in a natural orifice entry site surgical procedure such as a TAMIS procedure such as a surgical access port sold as a GELPOINT path system. Certain aspects of the GELPOINT path system are described in U.S. Pat. Nos. 9,289,115 and 9,289,200, each issued Mar. 22, 2016, each entitled "NATURAL ORIFICE SURGERY SYSTEM," each of which are incorporated herein by reference in their entireties. In general, the surgical site access system 900 can comprise a pressure conditioning apparatus 70, a surgical access port 902 having a port surface 904, and a plurality of trocars 930, 940 configured to be advanced through the port surface 904 and to sealingly engage surgical instruments inserted therethrough.

With continued reference to FIG. 3, in some embodiments, the surgical access port 902 can comprise at least one insufflation port 910, 920. In some embodiments of surgical site access system 900, the pressure conditioning apparatus 70 can be fluidly coupled to one of the insufflation ports 910, 920. The other of the insufflation ports 910, 920 can then either be left free and remain closed with a stopcock valve or other closure device, be coupled to another source of gas, or be selectively opened to provide smoke evacuation for electrosurgical procedures.

With continued reference to FIG. 3, in some embodiments, the surgical site access system 900 can further comprise an insufflation trocar 940. The pressure conditioning apparatus 70 can be fluidly coupled to the insufflation trocar 940 and the trocar 940 advanced through the artificial body 904 wall to provide insufflation gas flow to the surgical site. The insufflation trocar 940 can comprise an instrument access channel 942 and an insufflation port 944. In certain embodiments, the insufflation port 944 of the insufflation trocar 940 can have a relatively large diameter relative to the insufflation ports 910, 920 of the surgical access port 902. In some embodiments, the insufflation port 944 of the insufflation trocar 940 can comprise a barbed fitting to receive the outlet gas tubing 94 of the pressure conditioning apparatus 70. Accordingly, the insufflation trocar 940 can desirably accommodate insufflation gas flow rates of a fluid coupling such as outlet tubing 94 of a pressure conditioning apparatus 70 having a relatively large inner diameter, such as the embodiment of FIG. 2.

The pressure conditioning apparatus 70 can be sized and configured to provide a desirable pressure conditioning profile for a surgical site at an open body conduit. For example, it can be desirable for the pressure conditioning apparatus to provide an insufflation gas flow having a relatively small lag time, and a relatively small pressure deviation. The lag time represents a time delay between activation of an insufflation pump fluidly coupled to the surgical site access system and reaching a desired insufflation pressure at the surgical site. The pressure deviation represents a pressure difference between a high pressure peak and a low pressure peak if insufflation pressure at the surgical site is plotted over time. Moreover, it can be desirable that the pressure conditioning apparatus be relatively compact such that it does not require a significant amount of operating room space.

Figure 4:
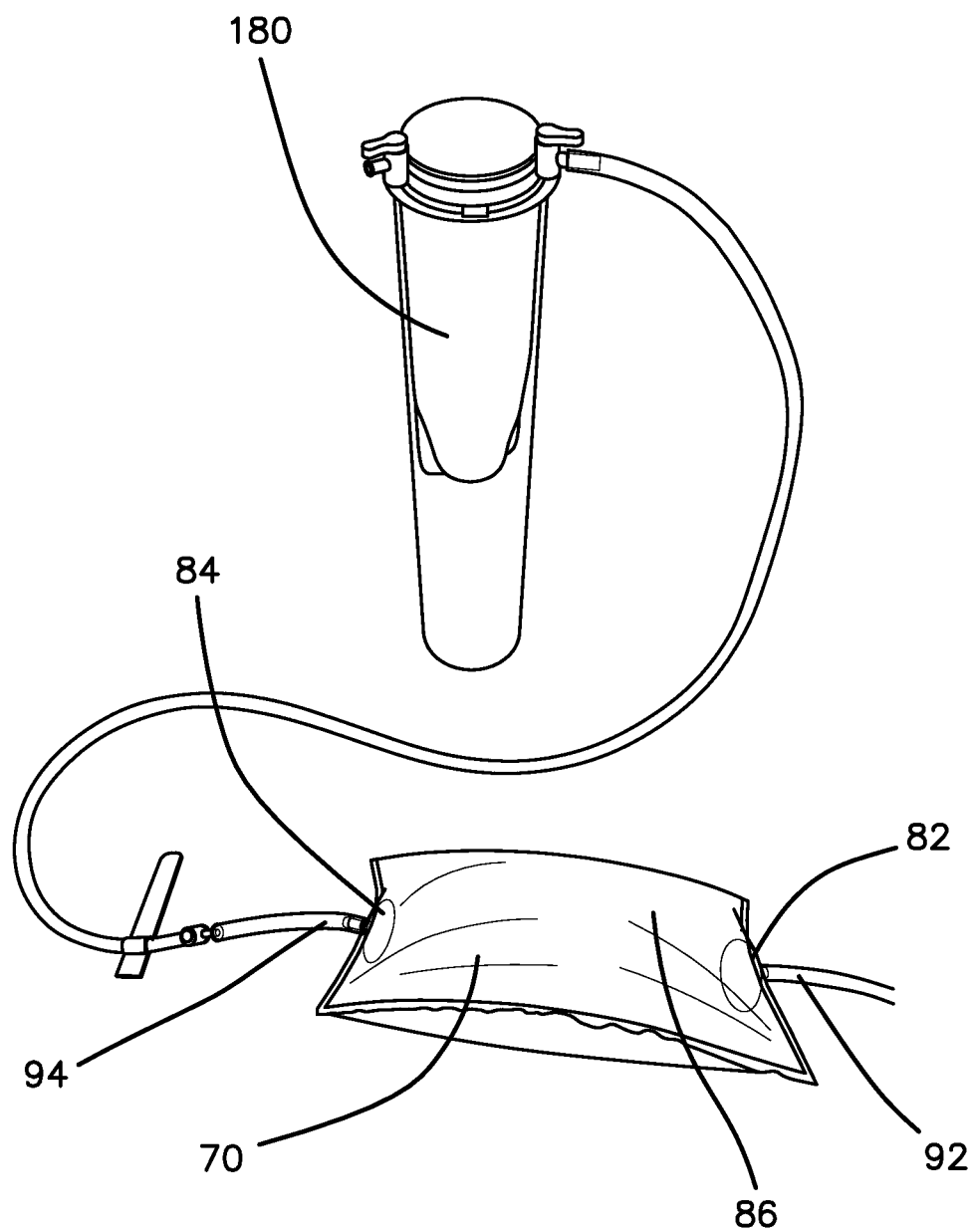
FIG. 4 is a perspective view of the pressure conditioning apparatus of FIG. 1 in an expanded configuration on a test fixture with a simulated body conduit.

With reference to FIG. 4, the insufflation gas pressure conditioning apparatus 70 of FIG. 1 is illustrated coupled to a test fixture including a distended simulated body conduit 180. The pressure conditioning apparatus 70 is illustrated with the pouch 86 in an inflated condition and a gas flow path (arrows showing flow direction) indicated from the inlet tube segment 92, through the pouch 86, through the outlet tube segment 94 and to the simulated body conduit 180. Desirably, a simulated body conduit 180, can be used to assess the conditioned pressure profile performance of various pressure conditioning apparatus 70 film pouch materials, thicknesses, volumes, and geometries as further discussed with reference to FIGS. 20-30.

Figure 5:
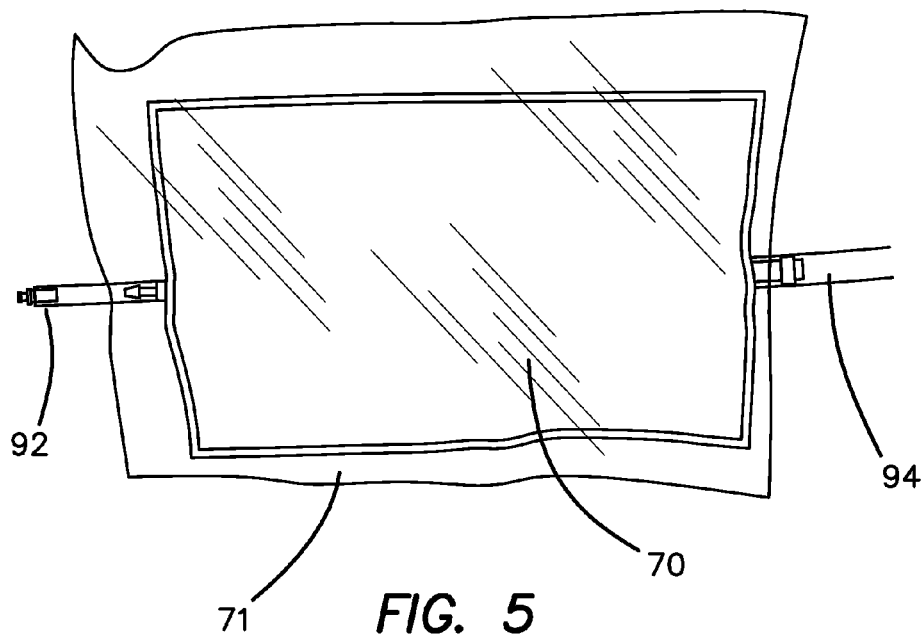
FIG. 5 is a side view of another embodiment of gas flow pressure conditioning apparatus.

With reference to FIG. 5, another embodiment of pressure conditioning apparatus 70 is illustrated. In the illustrated embodiment, a film pouch, such as that of FIGS. 1-4 can be positioned within an outer envelope 71. The outer envelope 71 can be sized to allow a predetermined amount of elastic and/or plastic deformation of the film pouch of the pressure conditioning apparatus 70 while preventing the film pouch and its associated seams from plastically deforming to a material yield or split-seam condition. Thus, insufflation gas flows from an inlet tube segment 92, through the pressure conditioning apparatus 70 through the outlet tube segment 94. As the pressure conditioning apparatus 70 inflates and expands, it can abut an inner surface of the outer envelope 71, which reduces or stops further expansion.

In some embodiments, the outer envelope 71 can comprise the same film material and thickness as the film pouch of the pressure conditioning apparatus 70. In other embodiments, it can be desirable that the outer envelope is formed of a different polymeric film material or a different thickness of the same material. For example, in some embodiments, the film pouch can be formed of a polyurethane film having a thickness of 0.003 inches and the outer pressure envelope can be formed of a polyurethane film having a thickness of 0.006 inches.

Figure 6:
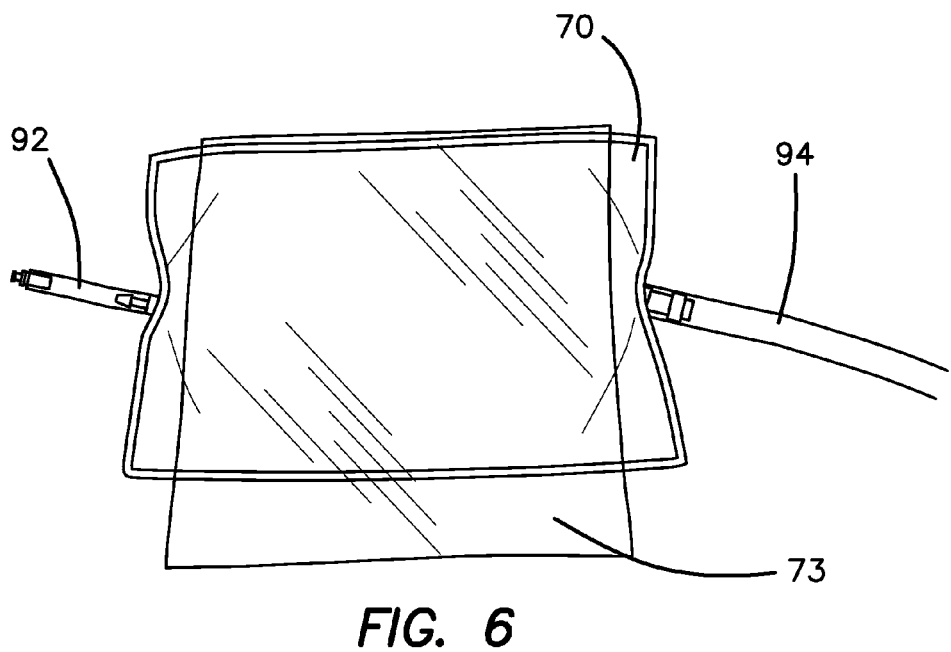
FIG. 6 is a side view of another embodiment of gas flow pressure conditioning apparatus.

With reference to FIG. 6, another embodiment of pressure conditioning apparatus 70 is illustrated. In the illustrated embodiment, a film pouch of the pressure conditioning apparatus is positioned within an outer sleeve 73. The outer pressure sleeve can have a generally tubular profile with open ends, through which the film pouch of the pressure conditioning apparatus 70 extends. As with the embodiment of FIG. 5, the outer pressure sleeve can allow a predetermined amount of elastic and plastic deformation of the pressure conditioning apparatus 70 while limiting the plastic deformation to prevent material yield or seam splitting when pressurized with an insufflation gas flow. The outer sleeve 73 can be joined to the film pouch of the pressure conditioning apparatus 70 such as by being heat welded along a seam of the film pouch. In the illustrated embodiment, the outer sleeve 73 is joined to the film pouch along one seam of the film pouch. In other embodiments, the outer sleeve can be joined at more than one seam of the film pouch or can be joined at other locations of the film pouch with a welded seam or with adhesives.

Figure 7:
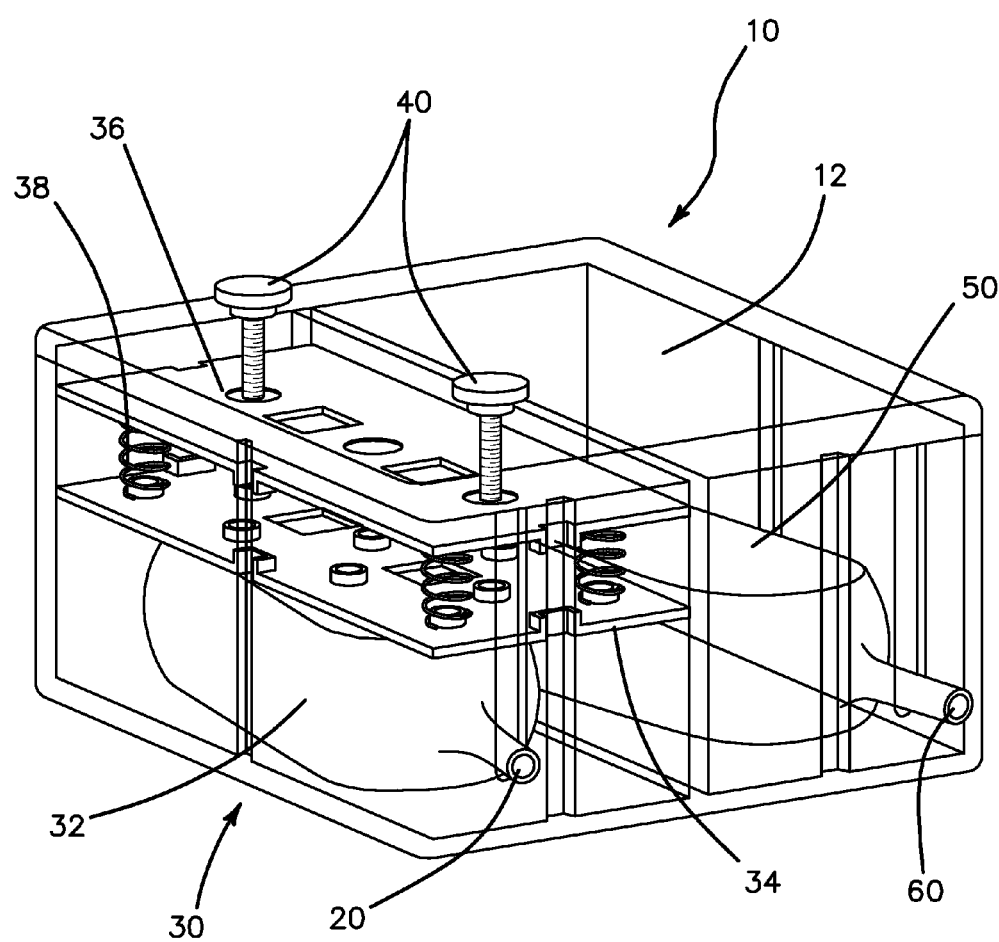
FIG. 7 is a perspective view of an embodiment of gas flow pressure conditioning apparatus.
Figure 8:
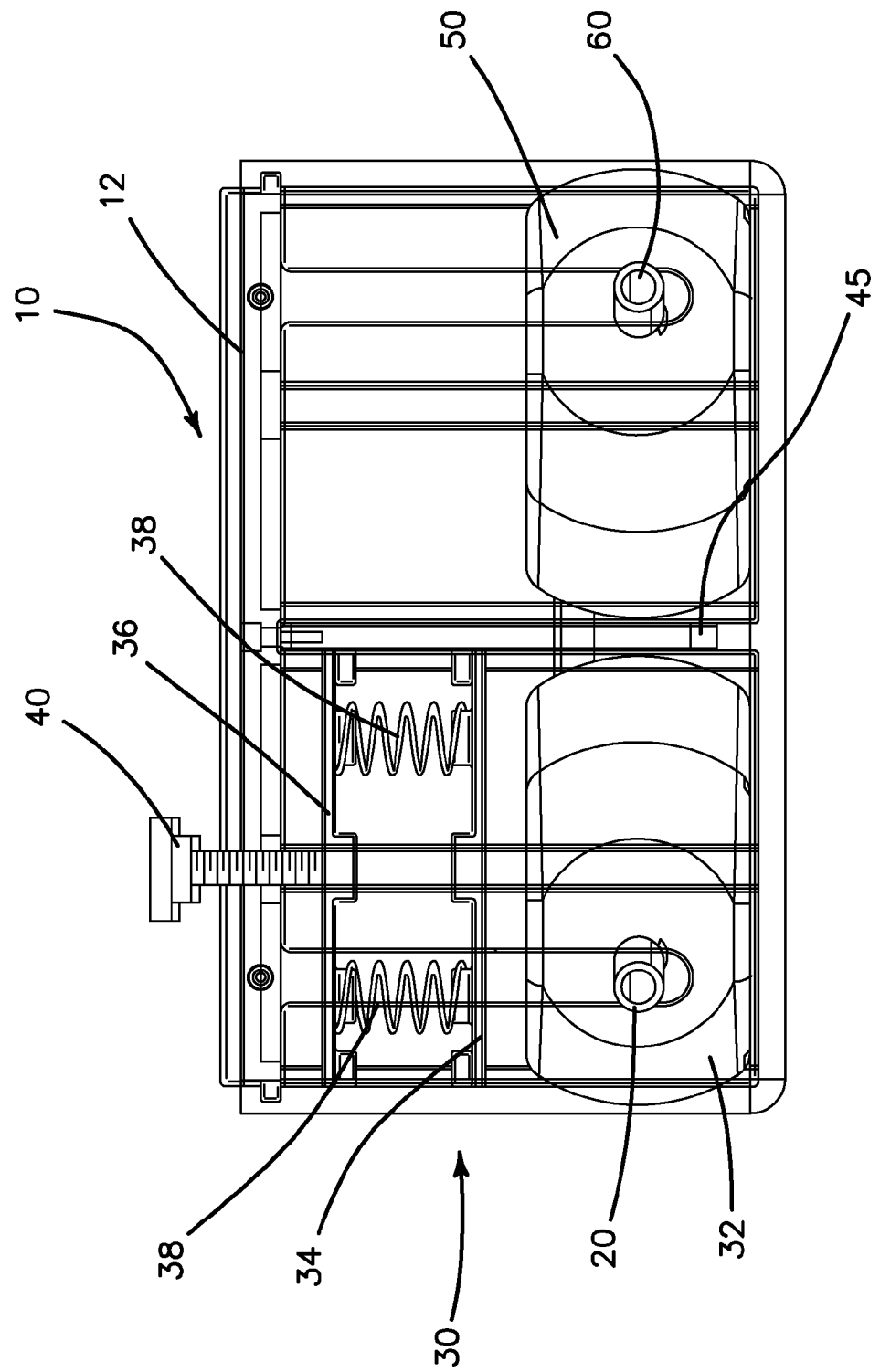
FIG. 8 is a front view of the pressure conditioning apparatus of FIG. 7.
Figure 9:
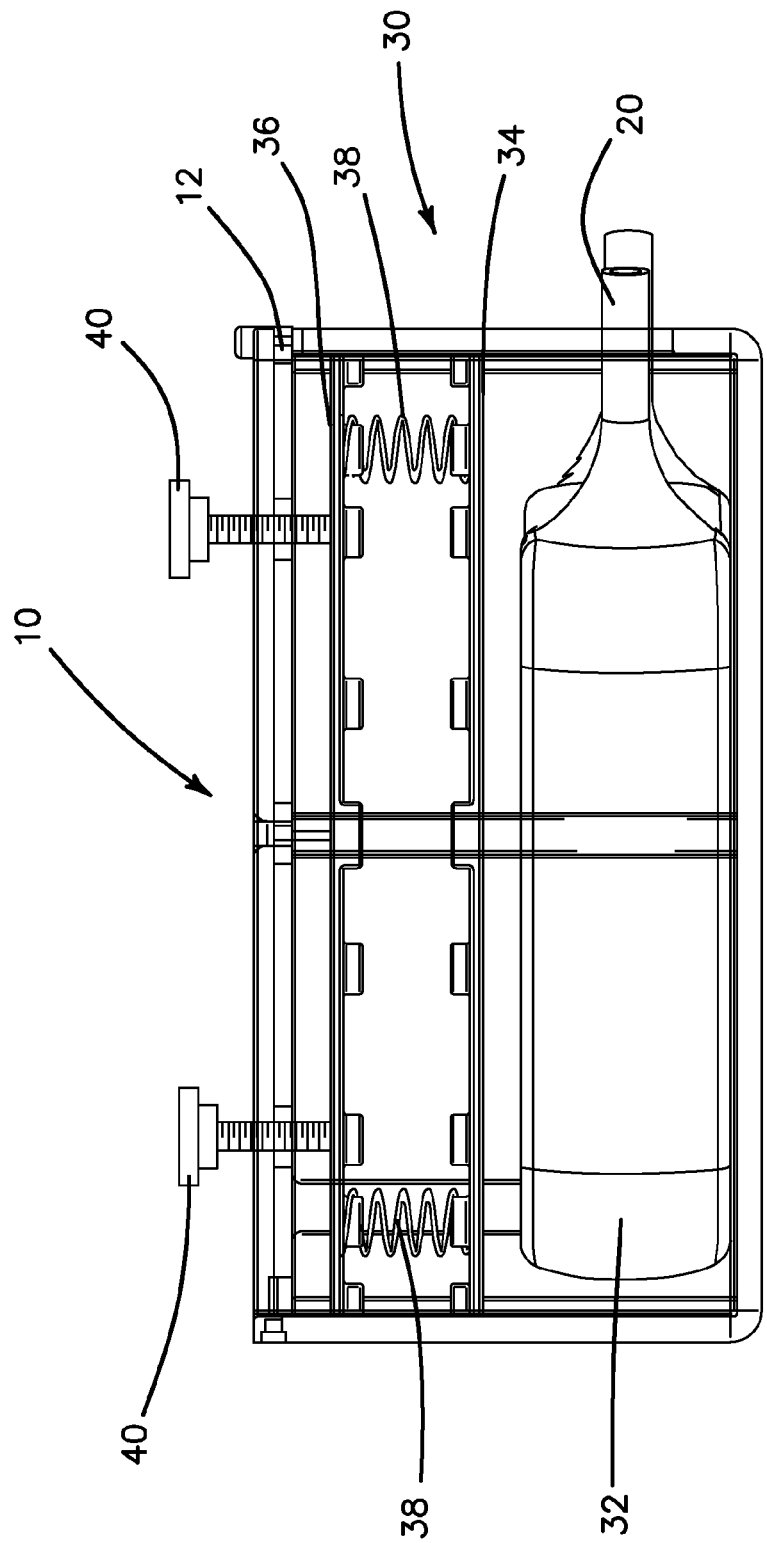
FIG. 9 is a side view of the pressure conditioning apparatus of FIG. 7.

With reference to FIGS. 7-9, perspective, front, and side views of another embodiment of gas flow pressure conditioning apparatus 10 are illustrated. In the embodiment of FIG. 7-9 the various pressure conditioning functions of pressure storage, volume accumulation, and flow rate restriction can each be provided by a dedicated component. In the illustrated embodiment, the pressure conditioning apparatus 10 includes a housing 12 enclosing or substantially enclosing components of the apparatus 10. The housing 12 can be sized and configured to fit on an equipment cart or rack for use in a medical facility. A fluid flow inlet port 20 and outlet port 60 can protrude from or be recessed into the housing 12. During a surgical procedure, the inlet port 20 can be fluidly coupled to an insufflation source, such as a pulsing insufflation pump. The pulsing insufflation pump can provide fluid flow in a non-continuous or pulsed stream. The outlet port 60 can be fluidly coupled to a surgical access port such as an insufflation channel on a trocar cannula, a single site minimally invasive surgical access port, or a natural orifice or transanal minimally invasive surgery access port.

With continued reference to FIGS. 7-9, in some embodiments, the housing 12 of the pressure conditioning apparatus 10 encloses a pressure storage component 30 and an accumulator 50. In some embodiments, the housing 12 can comprise an internal wall that forms separate compartments for each of the pressure storage component 30 and the accumulator 50. The pressure storage component 30 and the accumulator 50 can be fluidly coupled to one another and to the inlet port 20 and outlet port 60 to create a fluid flow path between the inlet port 20 and the outlet port 60. For example, a segment of gas flow tubing 45 can fluidly couple the pressure storage component 30 to the accumulator 50. As further described with respect to FIGS. 18A-18D, in some embodiments the segment of gas flow tubing 45 can be fluidly coupled to a flow restrictor to further condition the gas flow therethrough. The flow restrictor can be configured to reduce the amplitude of pulses generated by an insufflation machine while lengthening the duration of the pulses. Accordingly, the flow restrictor can condition a pulsed insufflation gas inflow to become closer to a continuous flow downstream of the flow restrictor.

With continued reference to FIGS. 7-9, in the illustrated embodiment, the pressure storage component 30 is downstream of the inlet port 20, the gas flow tubing 45 is downstream of the pressure storage component, the accumulator 50 is downstream of the gas flow tubing 45, and the outlet 60 is downstream of the accumulator 50. It is contemplated that in other embodiments other arrangements of components can be used. For example, in some embodiments, a pressure conditioning apparatus 10 can comprise an accumulator positioned upstream of a pressure storage component and the pressure storage component positioned upstream of a flow restrictor relative to the fluid flow path. In other embodiments, a pressure conditioning apparatus 10 can comprise a flow restrictor positioned upstream of a pressure storage component and the pressure storage component positioned upstream of an accumulator relative to the fluid flow path.

Furthermore, in the illustrated embodiment, the pressure storage component 30, the gas flow tubing 45, and the accumulator 50 are fluidly coupled in series between the inlet port 20 and the outlet port 60. In other embodiments, it is contemplated that various arrangements of parallel or side branch fluid couplings can be included with pressure conditioning apparatuses.

The pressure storage component is capable of receiving, storing and returning pressurized insufflation gas such as $CO_2$ such that the returned $CO_2$ is at substantially the same pressure as the received $CO_2$. Additionally, the pressure storage component can desirably be able to return pressurized $CO_2$ relatively quickly. For example, in some embodiments it is desirable that the pressure storage component is configured to maintain a pressure of an insufflation gas flow upon cessation of an insufflation pulse or relief of backpressure from the surgical site in less than approximately 10% of the time that a pulsing insufflation machine would be in a pressurize cycle. Advantageously, the pressure storage component 30 in conjunction with the pressure conditioning apparatus 10 can be configured to quickly vary the flow rate of insufflation gas at the outlet port 60 to counteract leakage and absorption of $CO_2$ at the surgical site downstream of the outlet. Thus, the pressure conditioning apparatus 10 can maintain a substantially constant pressure at the surgical site.

As illustrated, the pressure storage component 30 comprises a vessel 32 or fluid reservoir and a pressure generating mechanism. The vessel 32 can be a flexible or elastomeric container having a variable internal volume defined by flexing or expansion of walls thereof between a first, relatively low volume state and a second, relatively high volume state. The pressure generating mechanism can bear on an outer wall of the vessel 32 to bias the vessel 32 towards the first, relatively low volume configuration to maintain a desired pressure of gas within the vessel 32 even when flow of gas at the inlet 20 is interrupted (e.g. between pressurized pulses from a pulsing insufflation pump) or backpressure is reduced from the outlet 60 (e.g. when insufflation gas escapes from a surgical site or is absorbed by tissue at the surgical site).

With continued reference to FIGS. 7-9, the pressure generating mechanism can comprise a first plate 34 bearing against a wall of the vessel 32, a second plate 36 bearing against the housing 12, and a biasing mechanism such as one or more coil springs 38 positioned between the first and second plates 34, 36 to generate a biasing force tending to separate the plates and compress the vessel 32. In the illustrated embodiment, the plates 34, 36 are generally rectangular and the biasing mechanism comprises four coil springs 38, with a coil spring 38 extending between the first and second plates 34, 36 adjacent each corresponding corner of the generally rectangular plates. In other embodiments, it is contemplated that more or fewer than four coil springs 38 can be positioned at various positions between the plates 34, 36.

The plates 34, 36 and the housing 12 can each comprise engagement surfaces to align the plates in a desired orientation within the housing to generate the biasing force in a desired direction relative to the housing 12 and the vessel 32. For example, in the illustrated embodiment, the plates 34, 36 each include a plurality of recesses or grooves positioned to engage with and slide along inwardly-protruding ribs in the housing 12.

In some embodiments, the pressure storage component 30 can comprise a pressure adjustment mechanism such as one or more threaded spacers 40 that can allow a user to adjust a position of the second plate 36 relative to the housing 12. Advancing the threaded spacers 40 to position the second plate 36 relatively deeply within the housing can provide a relatively high biasing force on the vessel 32 generated by the pressure generating mechanism. Alternatively, retracting the threaded spacers 40 to position the second plate 36 relatively close to an upper surface of the housing can provide a relatively low biasing force on the vessel 32 generated by the pressure generating mechanism. In the illustrated embodiment, the threaded spacers 40 each comprise a threaded shaft having a proximal end with an adjustment knob thereon and a distal end positioned against the second plate 36. The threaded shafts engage corresponding threaded apertures formed in the upper surface of the housing 12.

With continued reference to FIGS. 7-9, as the insufflation gas flows downstream from the pressure storage component 30, it passes through the gas flow tubing 45 with its flow restrictor to further condition a pulsed profile of the insufflation gas flow and in to the accumulator 50. The accumulator 50 can provide a reservoir of insufflation gas, pressurized by the pressure storage component 30, that can stabilize a pressure at a surgical site fluidly coupled to the outlet port 60 between pulses of the insufflation machine.

In certain embodiments, the accumulator 50 can comprise a flexible or rigid vessel or reservoir. The accumulator 50 can be sized with a volume that can retain a predetermined percentage of a volumetric rating of the insufflation pump such that the system maintains a substantially constant pressure at the surgical site. For example, desirably, the accumulator can have a volume that contains from approximately 10%-20% of the volumetric rating of the insufflation machine. Preferably, the accumulator can have a volume that contains approximately 15% of the volumetric rating of the insufflation machine.

Figure 10:
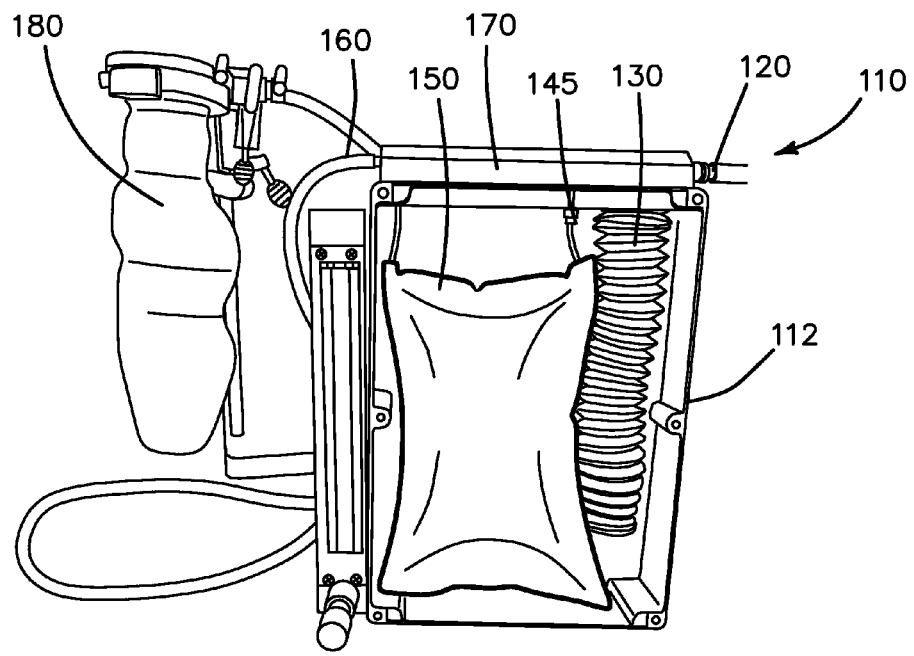
FIG. 10 is a side view of another embodiment of gas flow pressure conditioning apparatus on a test fixture.

With reference to FIG. 10, a side view of another embodiment of insufflation gas pressure conditioning apparatus 110 is illustrated. In the illustrated embodiment, the conditioning apparatus 110 comprises a gas flow path extending from an inlet port 120 to an outlet port 160, with the outlet port 160 illustrated as being fluidly coupled to a distended simulated body conduit 180 on a test fixture. The inlet port 110 is fluidly coupled to a gas conduit 170. The pressure conditioning apparatus 110 includes a pressure storage component 130, a flow-restricting gas tube 145, and an accumulator 150 fluidly coupled to the gas conduit 170. The various components of the pressure conditioning apparatus 110 operate substantially as described above with respect to the pressure conditioning apparatus of FIGS. 7-9.

With continued reference to FIG. 10, in the illustrated embodiment, the pressure storage component 130 comprises a vessel having a bellows configuration. The bellows is expandable responsive to gas pressure, but is biased towards a relatively low volume, contracted configuration. In the illustrated embodiment, the accumulator 150 comprises a pouch having a predetermined volume. The pouch can be formed of a film of a polymeric material, such as a polyurethane film. The pressure storage component 130, gas tube 145, and accumulator 150 can be housed within a housing 112 similar to that of the embodiment of FIGS. 7-9.

Figure 11:
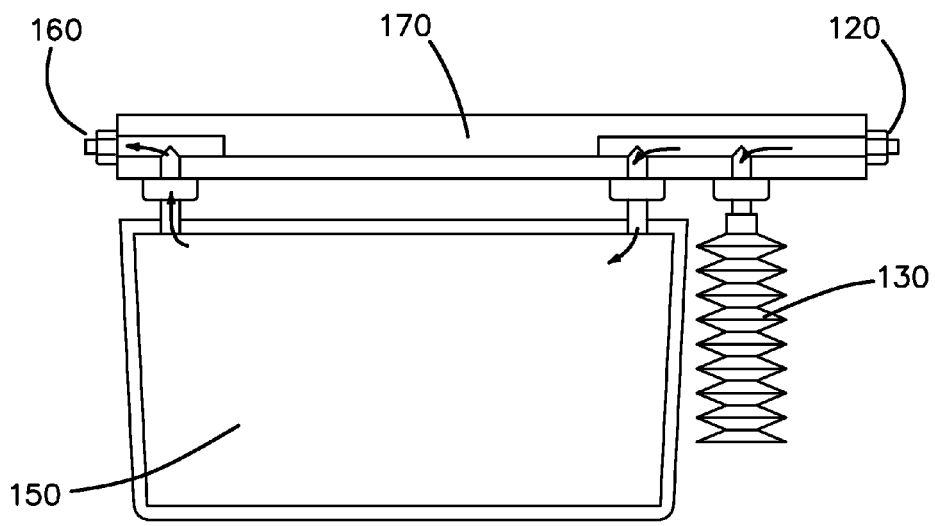
FIG. 11 is a schematic view of the gas flow pressure conditioning apparatus of FIG. 10.
Figure 12:
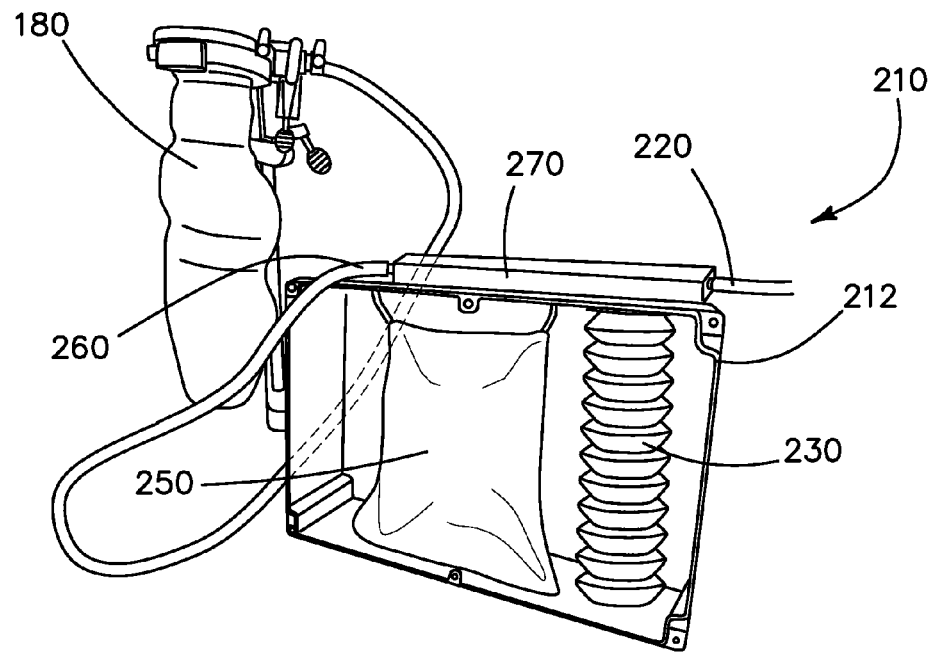
FIG. 12 is a side view of another embodiment of gas flow pressure conditioning apparatus on a test fixture.

With reference to FIG. 11, a schematic view of the pressure conditioning apparatuses of FIGS. 10 and 12 is illustrated. As illustrated, the pressure storage component 130 extends from a side branch of the gas conduit 170 that extends from the inlet port 120 to the outlet port 160. Accordingly, in various embodiments of pressure conditioning apparatus described herein, the components can be disposed in various flow arrangements including serial and side branch arrangements to maintain a desired pressure profile at a surgical site.

With reference to FIG. 12, a side view of another embodiment of gas flow pressure conditioning apparatus 210 is illustrated. The apparatus of FIG. 12 is substantially similar to that of FIG. 10 with a housing 212 containing a pressure storage component 230 and accumulator 250. A gas flow conduit 270 can fluidly couple the pressure storage component 230 and accumulator 250 to an inlet port 220 and outlet port 260. In the illustrated embodiment, the housing 212 is sized to have a reduced height footprint as compared with housing 112 of the embodiment of FIG. 10. Accordingly, the materials, volumes, and biasing properties of the pressure storage component 230 and accumulator 250 can be selected to maintain a desired insufflation pressure profile.

Figure 13:
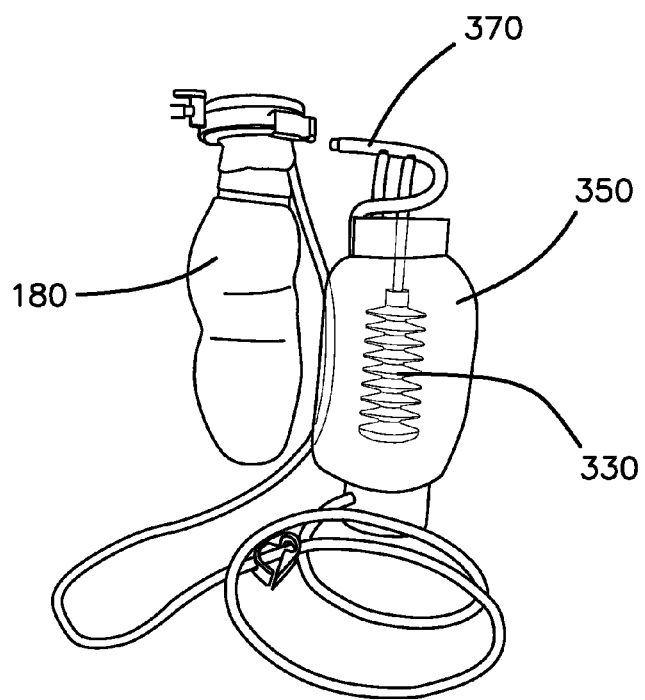
FIG. 13 is a side view of another embodiment of gas flow pressure conditioning apparatus on a test fixture.

With reference to FIG. 13, a side view of another embodiment of gas flow pressure conditioning apparatus is illustrated. The apparatus of FIG. 13 is substantially similar to that of FIGS. 10 and 12, however a pressure storage component 330 and accumulator 350 are not positioned within a housing. A gas flow conduit 370 can fluidly couple the bellows-profile pressure storage component 330 and accumulator 350 to an inlet port and outlet port that is coupled to a simulated body conduit 180.

Figures 14, 17:
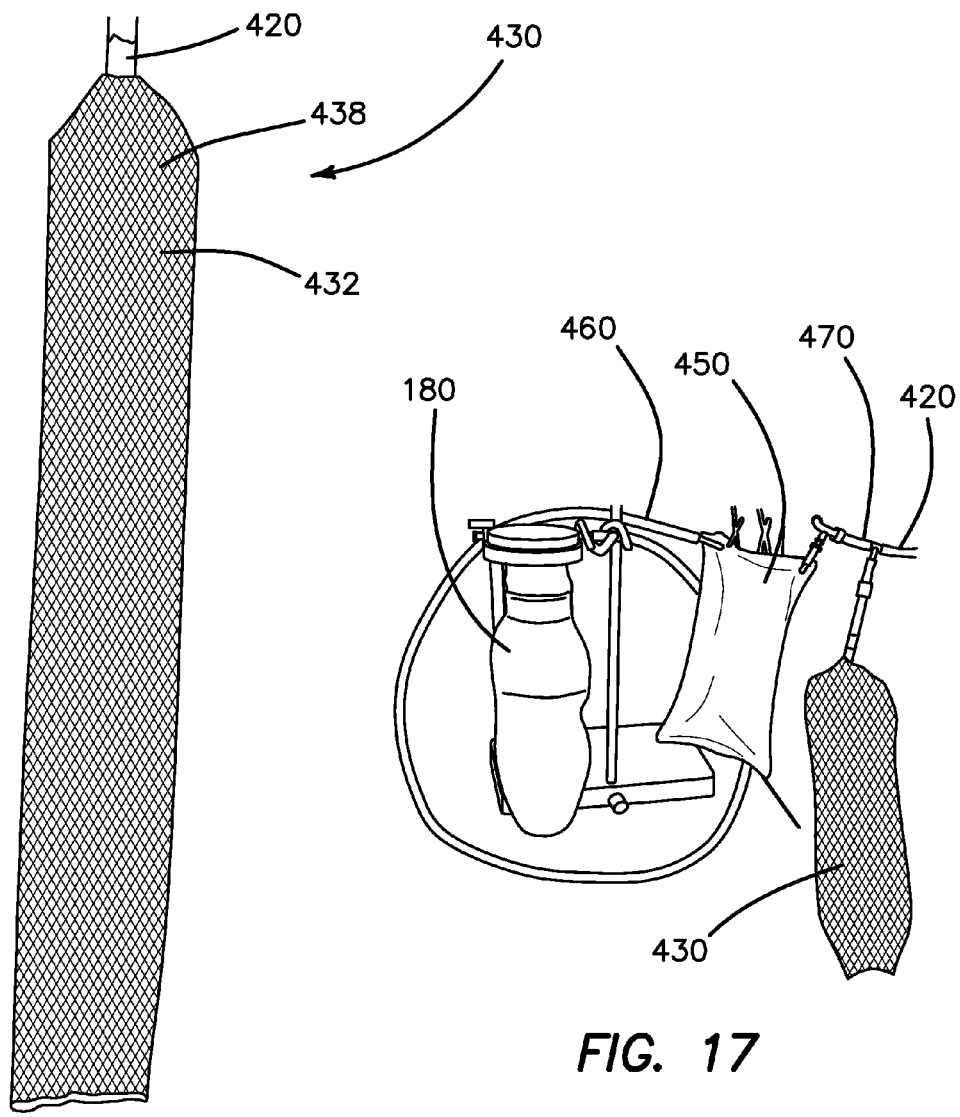
FIG. 14 is a perspective view of one embodiment of a pressure storage component for a pressure conditioning apparatus.
FIG. 17 is a side view of another embodiment of gas flow pressure conditioning apparatus on a test fixture.
Figure 15:
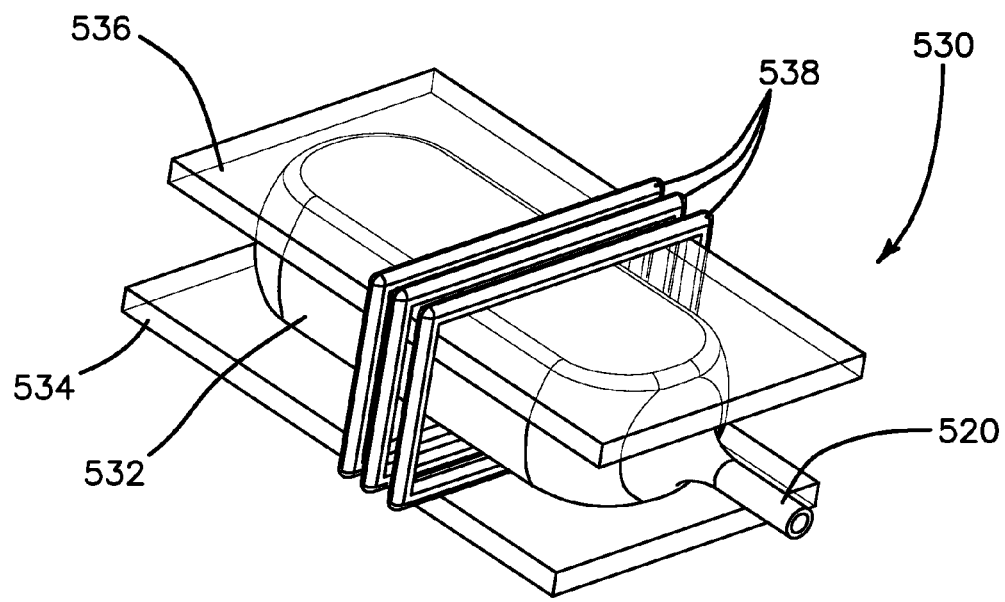
FIG. 15 is a perspective view of another embodiment of pressure storage component for a pressure conditioning apparatus.
Figure 16:
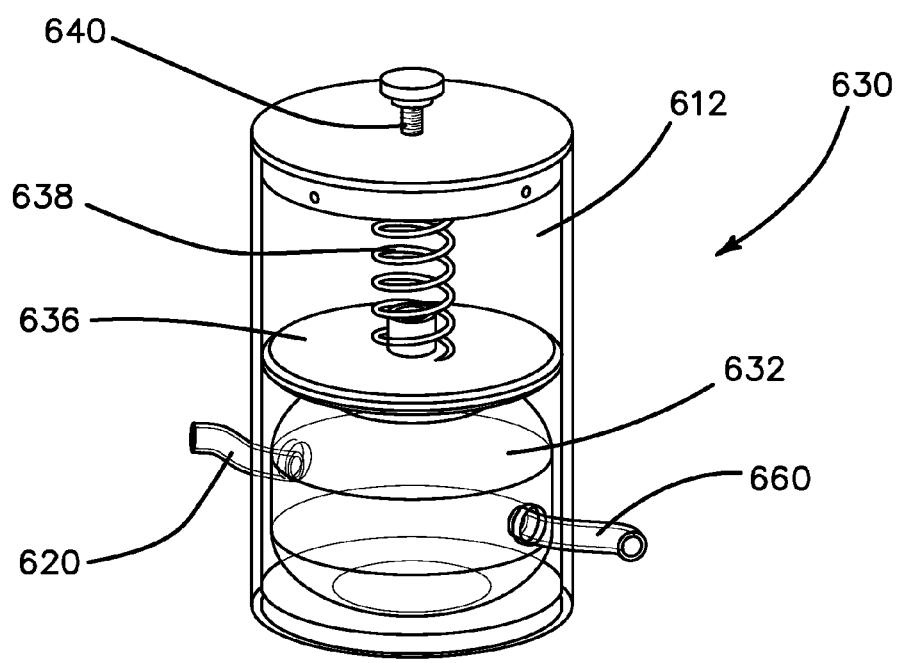
FIG. 16 is a perspective view of another embodiment of pressure storage component for a pressure conditioning apparatus.

With reference to FIGS. 14-16, various embodiments of a pressure storage component 430, 530, 630 are illustrated. In each of the illustrated embodiments, the pressure storage component 430, 530, 630 can comprise a reservoir or vessel 432, 532, 632. The reservoir 432, 532, 632 can have a variable volume, and a pressure generating mechanism can bias the reservoir 432, 532, 632 to a relatively low volume state.

With reference to FIG. 14, the illustrated pressure storage component 430 comprises a polymeric pouch reservoir 432 having a compression sleeve 438 encircling a portion thereof. The compression sleeve 438 comprises an elastic mesh that biases the reservoir 432 to a relatively low volume configuration to store and return pressure from a port 420 of the pressure storage component 430.

With reference to FIG. 15, the illustrated pressure storage component 530 can comprise a reservoir 532 that is sandwiched by compression members or plates 534, 536 that are biased towards one another to compress the reservoir 532 towards a relatively low volume configuration. The plates 534, 536 are biased towards one another by one or more compression bands 538. The pressure storage component 530 can have a single fluid port 520 to be fluidly coupled to a pressure conditioning apparatus as a side branch. In some embodiments, a pressure storage component 530 can further comprise a second port such that the reservoir 532 can comprise an inlet port and an outlet port.

With reference to FIG. 16, the illustrated pressure storage component 630 can comprise a reservoir 632 that is housed within a housing or canister 612. A compression plate 636 can bear on a wall of the reservoir 632 to compress the reservoir against an inner wall of the canister 612. The compression plate 636 can be coupled to the canister 612 by a coil spring 638. A position of the compression plate 636 relative to the housing, and therefore a biasing force generated thereby, can be adjusted by an adjustment mechanism such as a threaded shaft 640. In some embodiments, the pressure storage component 630 can be configured with an inlet port 620 and outlet port 660 for fluid coupling in a pressure conditioning apparatus in series.

With reference to FIG. 17, a side view of another embodiment of gas flow pressure conditioning apparatus is illustrated. The apparatus of FIG. 17 is substantially similar to that of FIG. 13, with no housing containing the pressure storage component 430 and accumulator 450. A gas flow conduit 470 can fluidly couple the pressure storage component 430 and accumulator 450 to an inlet port 420 and outlet port 460 that is coupled to a simulated body conduit 180. The pressure storage component 430 comprises a polymeric film pouch that is compressed by an expandable mesh as further described with reference to FIG. 14.

Figure 18A:
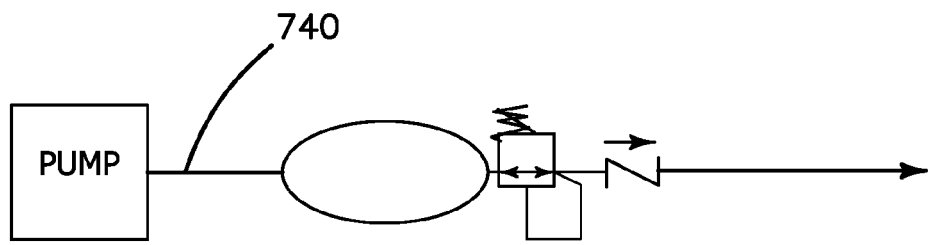
FIG. 18A is a schematic view of one embodiment of insufflation system.
Figure 18B:
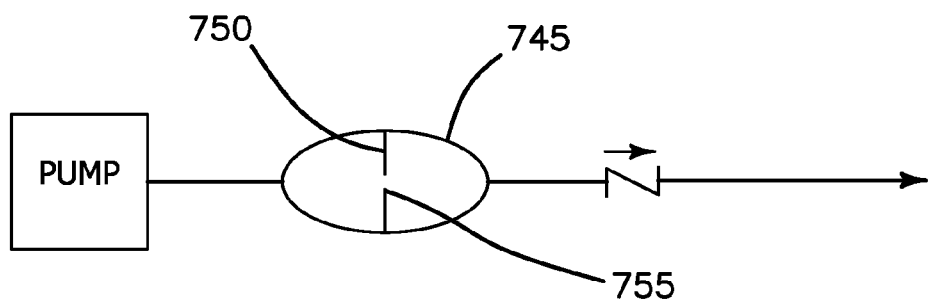
FIG. 18B is a schematic view of another embodiment of insufflation system having a flow restricting orifice.
Figure 18C:
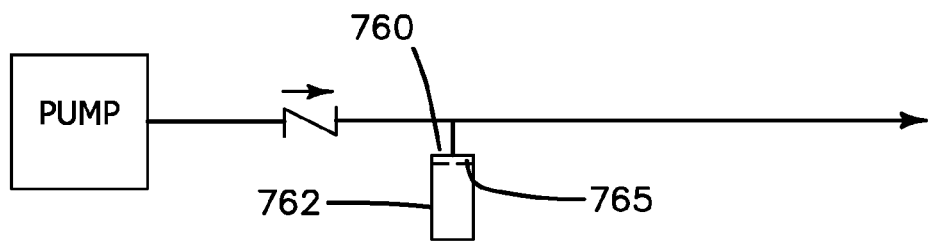
FIG. 18C is a schematic view of another embodiment of insufflation system having a side branch attenuator.
Figure 18D:
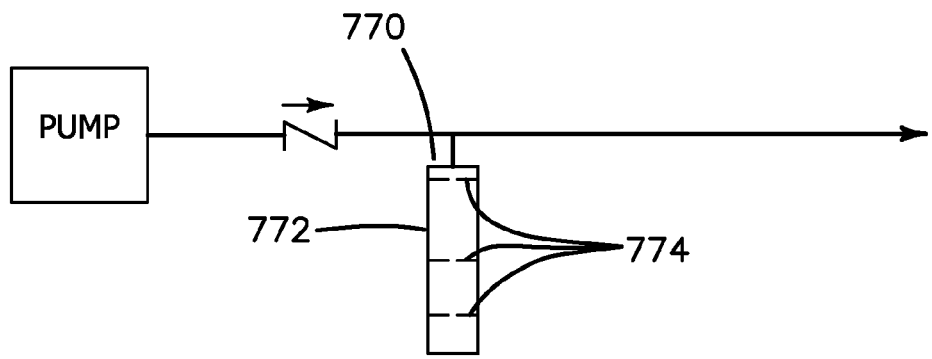
FIG. 18D is a schematic view of another embodiment of insufflation system having a Helmholtz resonator.

With reference to FIGS. 18A-18D, various embodiments of flow restrictor 750, 760, 770 for use with the pressure conditioning apparatuses described herein are schematically illustrated. As noted above with respect to FIGS. 7-9, in some embodiments, a flow restrictor can be serially coupled in a pressure conditioning apparatus between a pressure storage component and an apparatus. Many insufflation pumps provide pulsing output having pressure pulses defined by an amplitude and a duration. One or more flow restrictors positioned in series within a gas conduit 740 or tube (FIG. 18B) or as a side branch (FIGS. 18C, 18D) can condition the pulsing output to reduce the amplitude and lengthen the duration of the pulses downstream of the flow restrictor. Accordingly, the pressure conditioning apparatuses described herein can comprise a flow restrictor to further condition the gas flow therethrough to maintain substantially constant pressure at an outlet of the apparatus despite a pulsed inflow. In some embodiments, the flow restrictor 750 comprises flow restrictor plate 750 with a relatively small diameter orifice 755 positioned in a relatively large diameter gas conduit or tube 745. (FIG. 18B). In other embodiments, the flow restrictor 760 comprises a side branch attenuator having a canister or tube 762 having a restrictor plate 765 therein with a relatively small diameter orifice. (FIG. 18C). The side branch attenuator tube 762 is fluidly coupled on a side branch of a flow conduit. In other embodiments, the flow restrictor 770 can comprise a Helmholtz resonator comprising a plurality of restrictor plates 774 with relatively small diameter orifices positioned within a tube 772 or canister fluidly coupled on a side branch of a flow conduit.

With reference to FIGS. 19A-19F it is contemplated that in various embodiments, the pressure conditioning apparatuses 810 described herein can be fluidly coupled to an insufflation pump 800 and fluidly coupled to an open-ended body conduit such as a patient's rectum 820 to define a surgical system configured to maintain a desired insufflation pressure profile. While FIGS. 19A-19F label the pressure conditioning apparatuses 810 as 'BAG', it is contemplated that the embodiments of surgical system schematically illustrated therein can incorporate the pouch-based pressure conditioning apparatus described with respect to FIGS. 1-4, any of the various other embodiments of pressure conditioning apparatus described herein, or another pressure conditioning apparatuses configured to maintain a desired insufflation pressure profile.

Figure 19A:
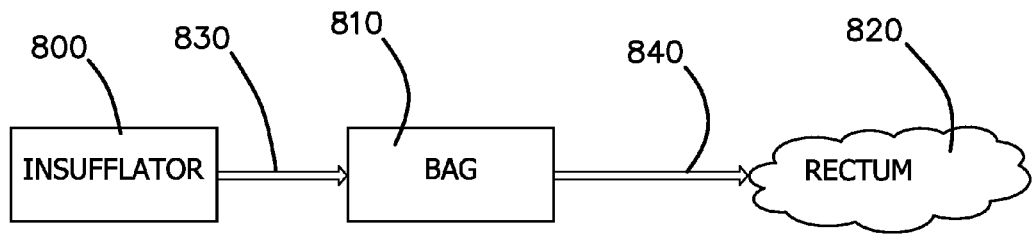
FIG. 19A is a schematic view of one embodiment of a surgical insufflation system including a gas flow pressure conditioning apparatus.

With reference to FIG. 19A, the illustrated embodiment of surgical system comprises a pressure conditioning apparatus 810 fluidly coupled to an insufflation pump 800 by a first fluid coupling 830 and fluidly coupled to a body conduit by a second fluid coupling 840. Arrowheads schematically illustrate a direction of fluid flow within the surgical system. In some embodiments, the first fluid coupling 830 and the second fluid coupling 840 can each comprise a segment of gas flow tubing such as are illustrated in FIG. 4. In some embodiments, the second fluid coupling 840 can be coupled to the body conduit at an insufflation port of a surgical access port such as a cannula or directly through an artificial body wall defined by a gel surface of a surgical access port sold under the trademarks GELPORT and GELPOINT.

With continued reference to FIG. 19A, in operation, the serial fluid coupling of the pressure conditioning apparatus 810 to the body conduit provided by the first fluid coupling 830 and second fluid coupling 840 of the surgical system result in mitigated pulsing or billowing of the body conduit despite pulsatile operation of the insufflation pump 800. The illustrated surgical system also generates a relatively lower pressure at the body conduit as compared with an insufflation pump directly coupled to a body conduit. This relatively low pressure results from the insufflation pump 800 sensing back pressure of the pressure conditioning apparatus 810 at the first fluid coupling 830. Typically, insufflation pumps 800 are configured to provide a pulsed insufflation profile responsive to pressure variations at a directly-coupled surgical site. However, the system volume added by the pressure conditioning apparatus 810 serially fluidly coupled to the body conduit and the insufflation pump 800 cause the insufflation pump 800 to generate a pulsatile pressure flow response to pressure variations at the first fluid coupling 830 of the system, which may differ from pressure at the body conduit.

Figure 19B:
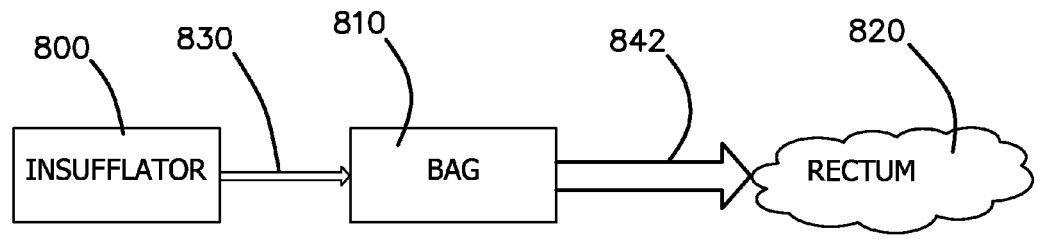
FIG. 19B is a schematic view of another embodiment of a surgical insufflation system including a gas flow pressure conditioning apparatus.

With reference to FIGS. 19B-19F, in various embodiments of surgical system, it can be desirable to reduce the pressure loss at a body conduit that tends to result from a serially-coupled pressure conditioning apparatus 810. With reference to FIG. 19B, the illustrated embodiment of surgical system comprises a pressure conditioning apparatus 810 fluidly coupled to an insufflation pump 800 by a first fluid coupling 830 and fluidly coupled to a body conduit by a second fluid coupling 842. The second fluid coupling 842 can have a thicker cross sectional profile defined by a relatively large inner diameter compared to standard insufflation tubing, which typically has a 0.25 inch inner diameter. This relatively large inner diameter of the second fluid coupling 842 increases the flow rate of insufflation gas from the pressure conditioning apparatus 810 to the body conduit, maintaining a relatively higher pressure in the body conduit than that of the embodiment of FIG. 19A.

Figure 19C:
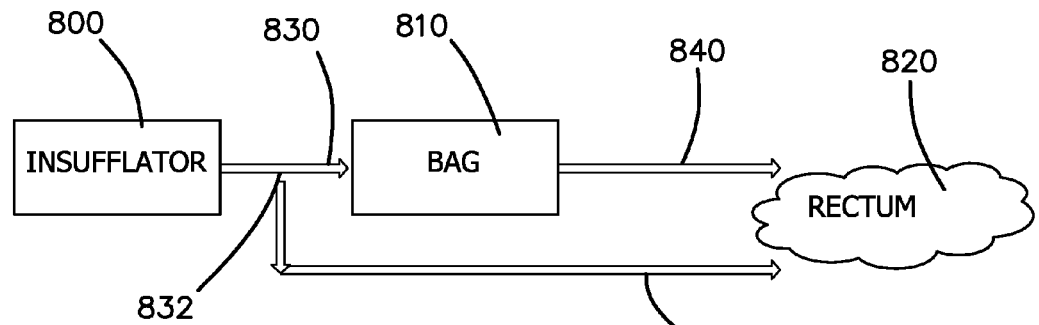
FIG. 19C is a schematic view of another embodiment of a surgical insufflation system including a gas flow pressure conditioning apparatus.

With reference to FIG. 19C, the illustrated embodiment of surgical system comprises a pressure conditioning apparatus 810 fluidly coupled to an insufflation pump 800 by a first fluid coupling 830 and fluidly coupled to a body conduit by a second fluid coupling 840. The first fluid coupling 830 can comprise a flow splitter such as a y-junction or y-valve to provide a dual lumen insufflation gas delivery pathway having a third fluid conduit 834 providing a parallel fluid flow path from the insufflation pump 800 to the body conduit. This dual lumen insufflation gas delivery pathway increases the flow rate of insufflation gas from the insufflation pump 800 to the body conduit, maintaining a relatively higher pressure in the body conduit than that of the embodiment of FIG. 19A.

Figure 19D:
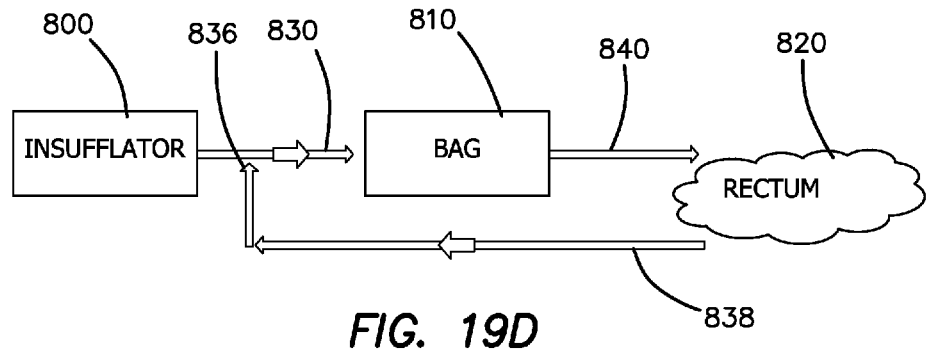
FIG. 19D is a schematic view of another embodiment of a surgical insufflation system including a gas flow pressure conditioning apparatus.

With reference to FIG. 19D, the illustrated embodiment of surgical system comprises a pressure conditioning apparatus 810 fluidly coupled to an insufflation pump 800 by a first fluid coupling 830 and fluidly coupled to a body conduit by a second fluid coupling 840. The first fluid coupling 830 can comprise a one-way valve 836 coupled to a parallel return lumen 838 that is fluidly coupled to the body conduit. This one-way valve 836 and return lumen 838 configuration provides backpressure feedback to the insufflation pump 800 while an insufflation gas delivery pathway is provided from the insufflation pump 800 through the pressure conditioning apparatus 810 to the body conduit, thus maintaining a relatively higher pressure in the body conduit than that of the embodiment of FIG. 19A.

Figure 19E:
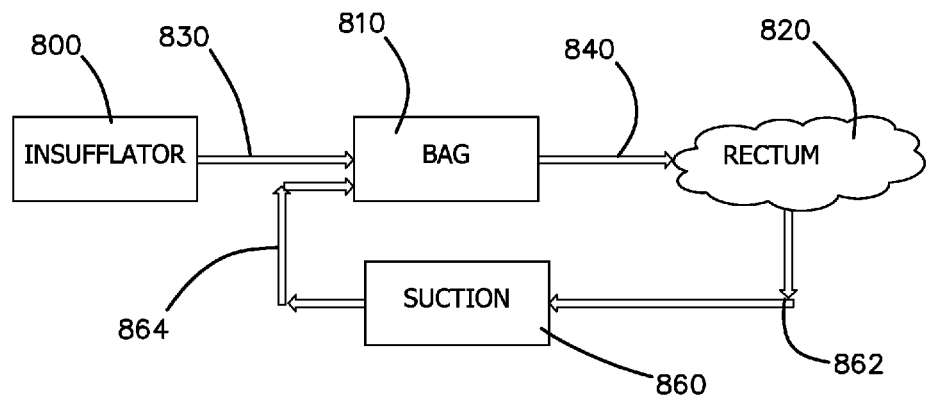
FIG. 19E is a schematic view of another embodiment of a surgical insufflation system including a gas flow pressure conditioning apparatus.

With reference to FIG. 19E, the illustrated embodiment of surgical system comprises a pressure conditioning apparatus 810 fluidly coupled to an insufflation pump 800 by a first fluid coupling 830 and fluidly coupled to a body conduit by a second fluid coupling 840. The surgical system further comprises a suction device 860 fluidly coupled to the body conduit by a first return conduit 862 and to the pressure conditioning apparatus 810 by a second return conduit 864, defining an insufflation gas return pathway. Thus, insufflation gas drawn out of the body conduit is reintroduced to the body conduit by way of the pressure conditioning apparatus 810. The gas return pathway can further comprise an in-line filter to prevent hazardous materials from re-entering the body conduit. This suction device 860 and return pathway can compensate for insufflation gas loss thus maintaining a desired pressure in the body conduit.

Figure 19F:
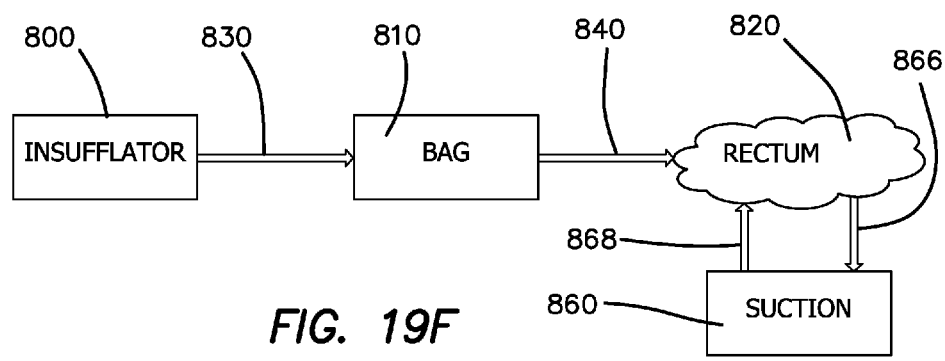
FIG. 19F is a schematic view of another embodiment of a surgical insufflation system including a gas flow pressure conditioning apparatus.

With reference to FIG. 19F, the illustrated embodiment of surgical system comprises a pressure conditioning apparatus 810 fluidly coupled to an insufflation pump 800 by a first fluid coupling 830 and fluidly coupled to a body conduit by a second fluid coupling 840. The surgical system further comprises a suction device 860 fluidly coupled to the body conduit by a first return conduit 866 and a reintroducing conduit 868, defining an insufflation gas return pathway that directly returns insufflation gas to the body conduit. Thus, insufflation gas drawn out of the body conduit is reintroduced to the body conduit by way of the reintroducing conduit 868. The gas return pathway can further comprise an in-line filter to prevent hazardous materials from re-entering the body conduit. This suction device 860 and return pathway can compensate for insufflation gas loss thus maintaining a desired pressure in the body conduit.

Figure 20:
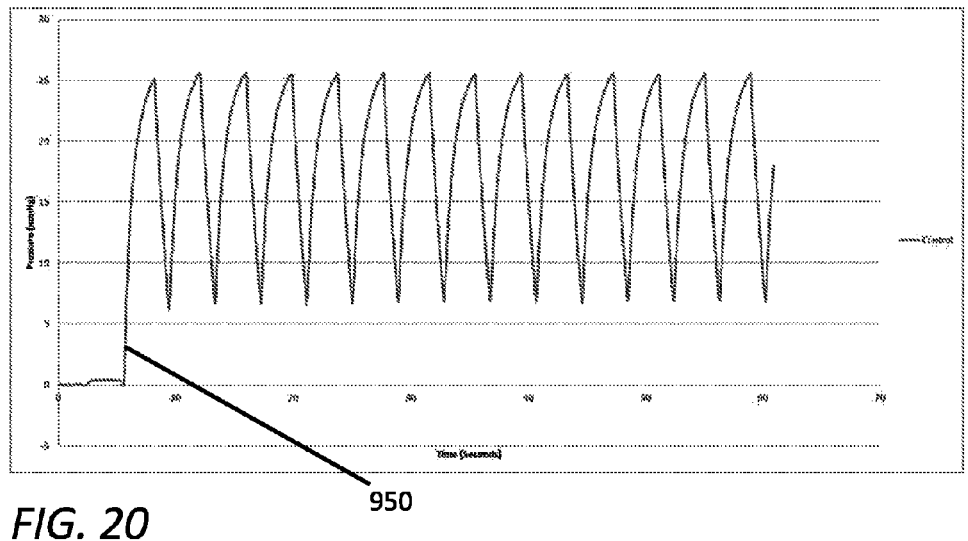
FIG. 20 is a graph of surgical site pressure over time for a simulated surgical access site insufflated with a pulsatile insufflation pump.

With reference to FIGS. 20-24, by assessing pressure conditioning performance over a series of simulated leakage tests including several embodiments of pressure conditioning apparatus, desirable configurations of the pressure conditioning apparatus can be identified. With reference to FIG. 20, baseline results in a test fixture of a simulated leak test including a silicone simulated rectum, a GELPOINT Path surgical access system and a standard pulsatile insufflator are illustrated. A pressure sensor was inserted into the simulated rectum to measure the internal pressure of the system. In a control setup, a GELPOINT Path stopcock was opened approximately half-way to create a leak rate of 10 L/min. The leak rate was kept consistent throughout subsequent tests of different embodiments of pressure conditioning apparatus of FIGS. 21-24. The insufflator was set at 15 mmHg, high flow. The insufflator turned on after 5 seconds.

FIG. 20 illustrates an exemplary observed pressure (in mmHg) at the simulated surgical site over time (in seconds). As illustrated, in the baseline or control configuration with no pressure conditioning apparatus, after an initial lag time of over 5 seconds, the baseline pressure plot 950 fluctuated between approximately 6 mmHg and approximately 25 mmHg, representing a pressure deviation of 19 mmHg. This fluctuation results in undesirable billowing of internal walls of the simulated body conduit.

Figure 21:
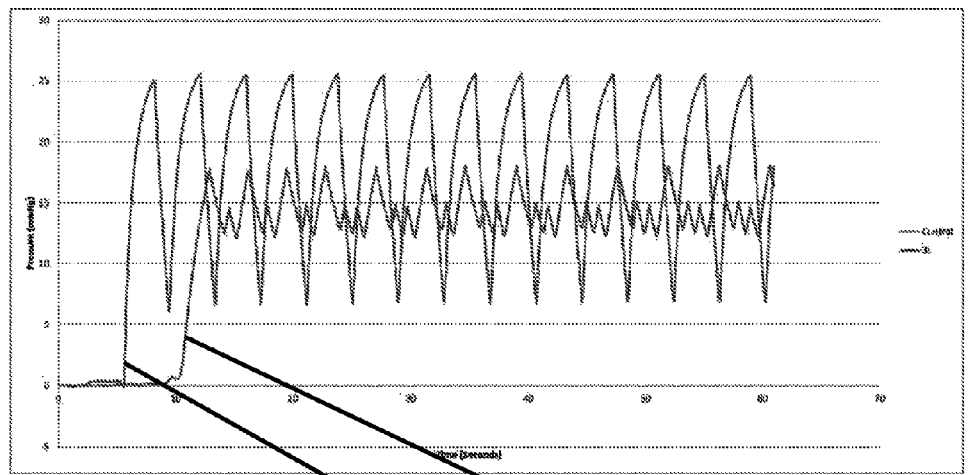
FIG. 21 is a graph of surgical site pressure over time for a simulated surgical access site insufflated with a pulsatile insufflation pump and an embodiment of pressure conditioning apparatus.
Figure 22:
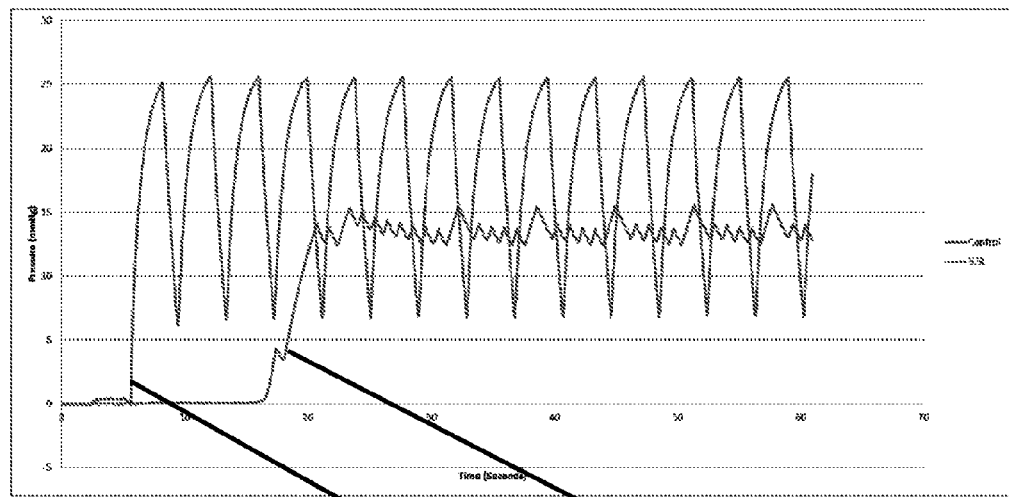
FIG. 22 is a graph of surgical site pressure over time for a simulated surgical access site insufflated with a pulsatile insufflation pump and another embodiment of pressure conditioning apparatus.
Figure 23:
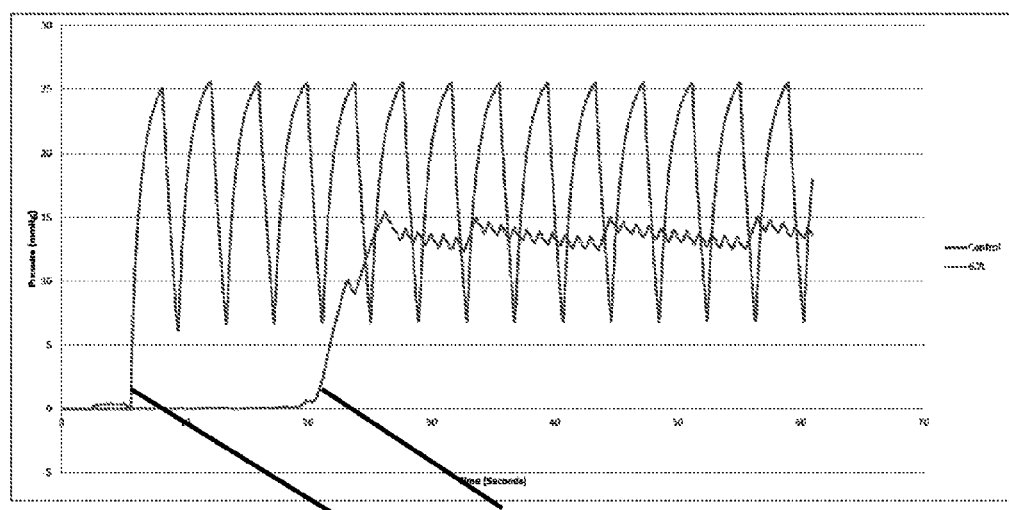
FIG. 23 is a graph of surgical site pressure over time for a simulated surgical access site insufflated with a pulsatile insufflation pump and another embodiment of pressure conditioning apparatus.
Figure 24:
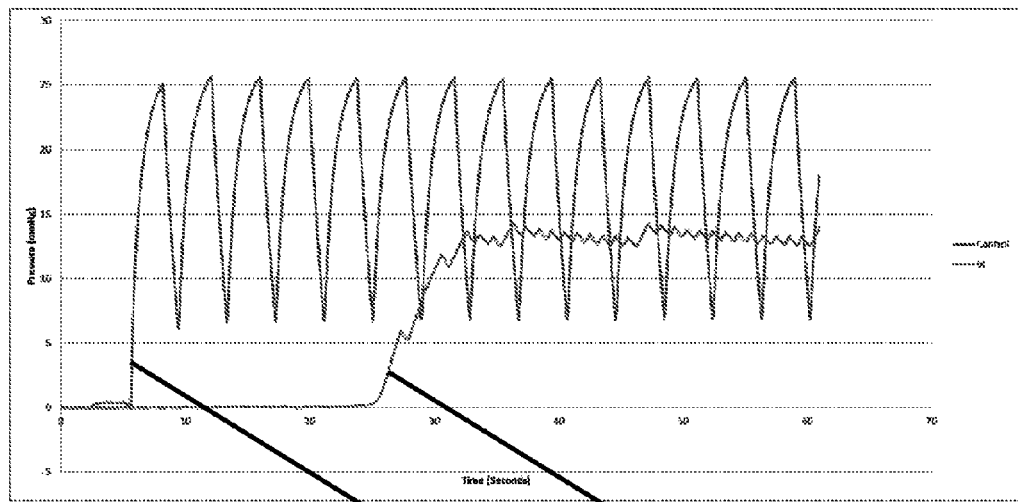
FIG. 24 is a graph of surgical site pressure over time for a simulated surgical access site insufflated with a pulsatile insufflation pump and another embodiment of pressure conditioning apparatus.

With reference to FIGS. 21-24, various embodiments of pressure conditioning apparatus were incorporated into a simulated surgical site access system for comparison with the baseline or control pressure plot. With reference to FIG. 21, a pressure plot 960 for a pressure conditioning apparatus including a reservoir having a volume of 3 L is plotted in comparison to the baseline pressure plot 950. As illustrated, the addition of the 3 L bag reduced the high to low pressure peak (deviation) to approximately 5 mmHg. With reference to FIG. 22, a pressure plot 962 for a pressure conditioning apparatus including a reservoir having a volume of 5.5 L is plotted in comparison to the baseline pressure plot 950. As illustrated, the addition of the 5.5 L reservoir reduced the pressure deviation to approximately 3 mmHg. With reference to FIG. 23, a pressure plot 964 for a pressure conditioning apparatus including a reservoir having a volume of 6.7 L is plotted in comparison to the baseline pressure plot 950. The addition of the 6.7 L reservoir reduced the pressure deviation to approximately 2.5 mmHg. With reference to FIG. 24, a pressure plot 966 for a pressure conditioning apparatus including a reservoir having a volume of 9 L is plotted in comparison to the baseline pressure plot 950. The addition of the 9 L reservoir reduced the pressure deviation down to approximately 2 mmHg.

With continued reference to FIGS. 21-24, while an increased reservoir volume desirably reduced the pressure deviation of the conditioned insufflation gas flow, the increased reservoir volume also tended to increase the lag time for the surgical site to achieve a desired insufflation pressure. For example, in the embodiments used in the simulated leakage tests, the observed lag times ranged from approximately 12 seconds (FIG. 21) to approximately 30 seconds (FIG. 24). Accordingly, in certain embodiments, it can be desirable that the reservoir be sized to provide a relatively low pressure deviation and a relatively low lag time. Moreover, it can be desirable that the reservoir be sized for ease of positioning and use in a surgical work environment. Accordingly, in some embodiments, the reservoir can have an internal volume between 5.5 and 8 liters. More desirably, the reservoir can have an internal volume of at least approximately 6.5 liters. In certain embodiments, the reservoir can have an internal volume of approximately 7.4 liters. Desirably, this range of volumes can provide a pressure deviation of under 3 mmHg, a lag time of under 30 seconds, and allow the bag to be positioned relatively easily in a surgical work environment.

Figure 25:
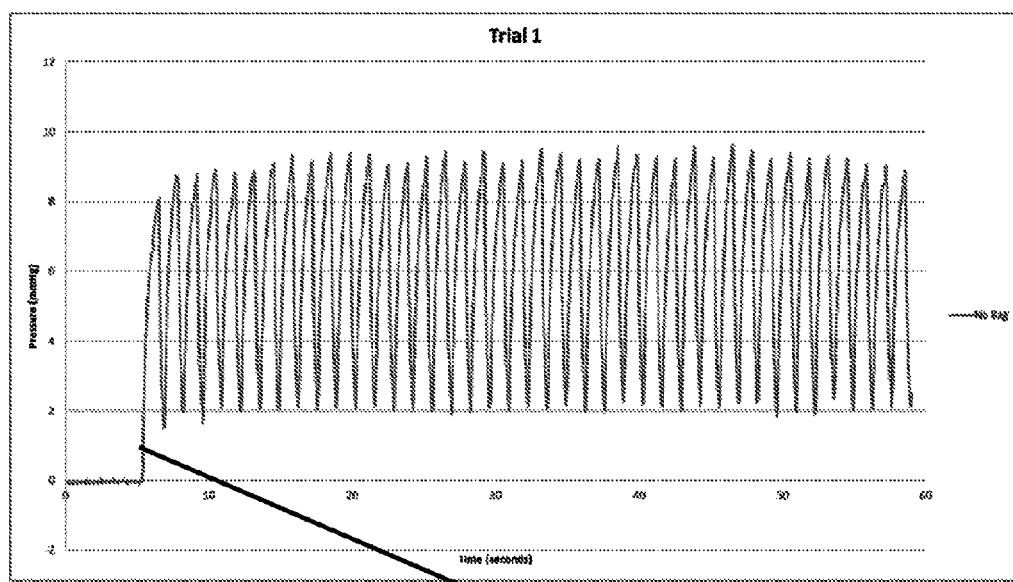
FIG. 25 is a graph of surgical site pressure over time for a simulated surgical access site in a cadaver laboratory setting insufflated with a pulsatile insufflation pump.
Figure 26:
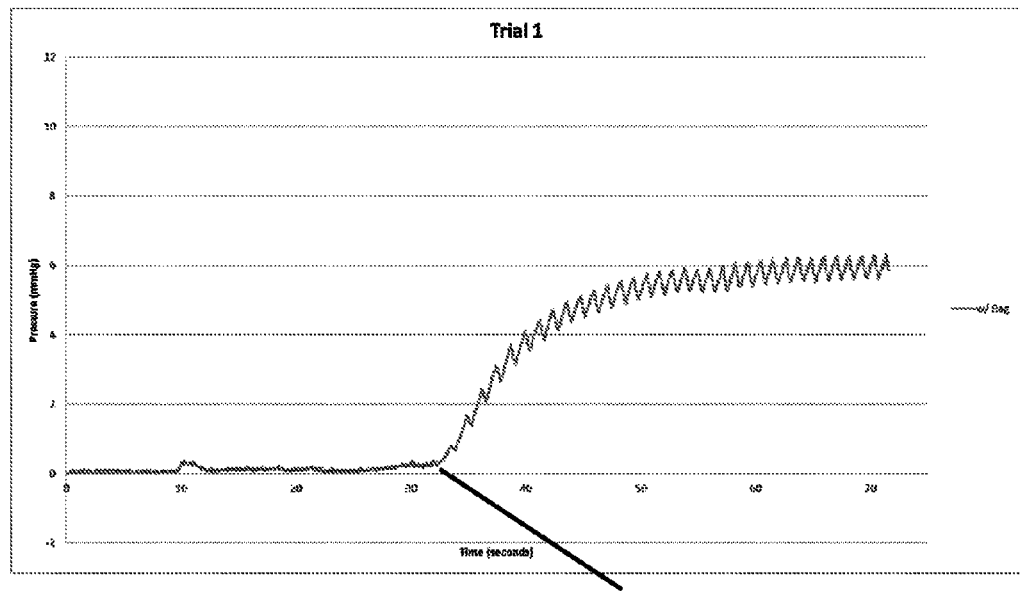
FIG. 26 is a graph of surgical site pressure over time for a simulated surgical access site of FIG. 25 insufflated with a pulsatile insufflation pump and an embodiment of pressure conditioning apparatus.

With reference to FIGS. 25-26, a pressure conditioning profile of a surgical site access system having a pressure conditioning apparatus with a reservoir having an internal volume of 6.5 liters was further verified on a human cadaver. In an experimental surgical access system setup, a stopcock on the surgical access port was opened to create a 7 L/min leak, the insufflator was set to a flow rate of 9 L/min, and insufflation pressure was set at 15 mmHg. In a control or baseline test, the rectal pressure fluctuated between 2 mmHg to 9 mmHg (pressure deviation of 7 mmHg). The control pressure plot 970, representing observed pressure at the simulated surgical site plotted over time, is illustrated in FIG. 25. The addition of the pressure conditioning apparatus having a reservoir with a volume of 6.5 liters reduced the pressure deviation to approximately 1 mmHg. FIG. 26 illustrates a pressure plot 972 for the surgical site access system with the pressure conditioning apparatus.

With reference to FIGS. 27-30, various embodiments of pressure conditioning apparatus having a reservoir with a volume of 6.5 liters were evaluated such that an inner diameter of an outlet tubing or fluid coupling can be sized and configured to provide a desirable pressure conditioning profile. The experimental setup included a simulated, silicone rectum, a GELPOINT Path surgical access system, a pressure conditioning apparatus having a reservoir such as is schematically illustrated in FIG. 2, and a pulsatile insufflator. The reservoir of the pressure conditioning apparatus used was 6.5 L in volume. The outlet tubing of the pressure conditioning apparatus was coupled to an insufflation trocar positioned through the surgical access system. A pressure sensor was inserted into the simulated rectum to measure the internal pressure of the system. In the control setup, a GELPOINT Path stopcock was opened approximately halfway to create a leak rate of 10 L/min, simulating insufflation gas losses and absorption from an open body conduit. The leak rate was kept consistent for all of the embodiments of the pressure conditioning apparatus. The insufflator was set at 15 mmHg, high flow. The insufflator turned on after 5 seconds. Outlet tubing of varying inner diameter sizes were tested, ranging from 0.1 inches to 0.5 inches. FIGS. 27-30 illustrate simulated surgical site pressure conditioning profiles for embodiments of pressure conditioning apparatus having different outlet tubing inner diameters.

Figure 27:
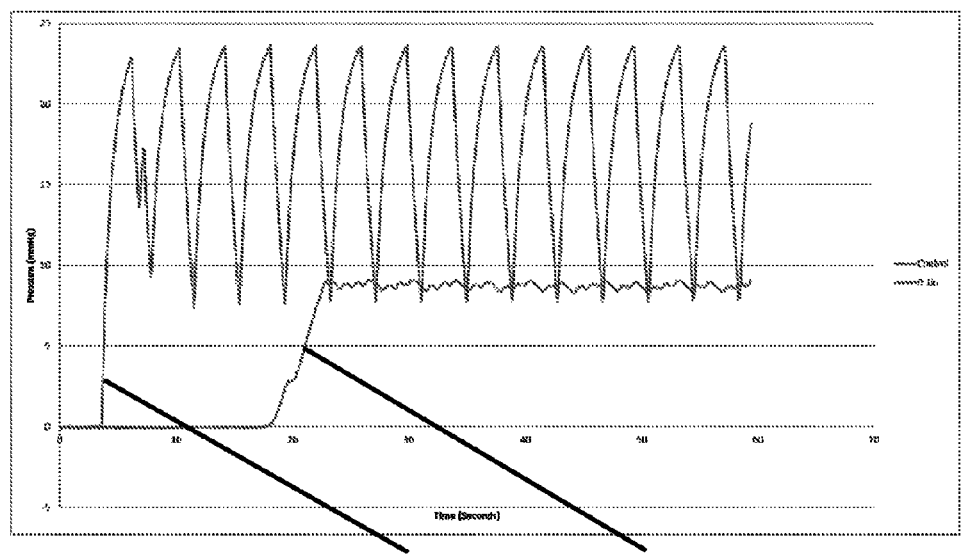
FIG. 27 is a graph of surgical site pressure over time for a simulated surgical access site insufflated with a pulsatile insufflation pump and an embodiment of pressure conditioning apparatus.

With reference to FIG. 27, a pressure plot 990 of a pressure conditioning apparatus having an outlet tubing with an inner diameter of 0.1 inches is illustrated in comparison to a baseline pressure plot 980 of the setup with no pressure conditioning apparatus. This embodiment of pressure conditioning apparatus maintained a pressure at the simulated surgical site of approximately 9 mmHg. Thus, the resulting pressure conditioning profile has a relatively high pressure drop, defined by the difference between the set pressure of the insufflator and the observed pressure at the surgical site. However, the pressure conditioning profile has relatively small pressure deviation.

Figure 30:
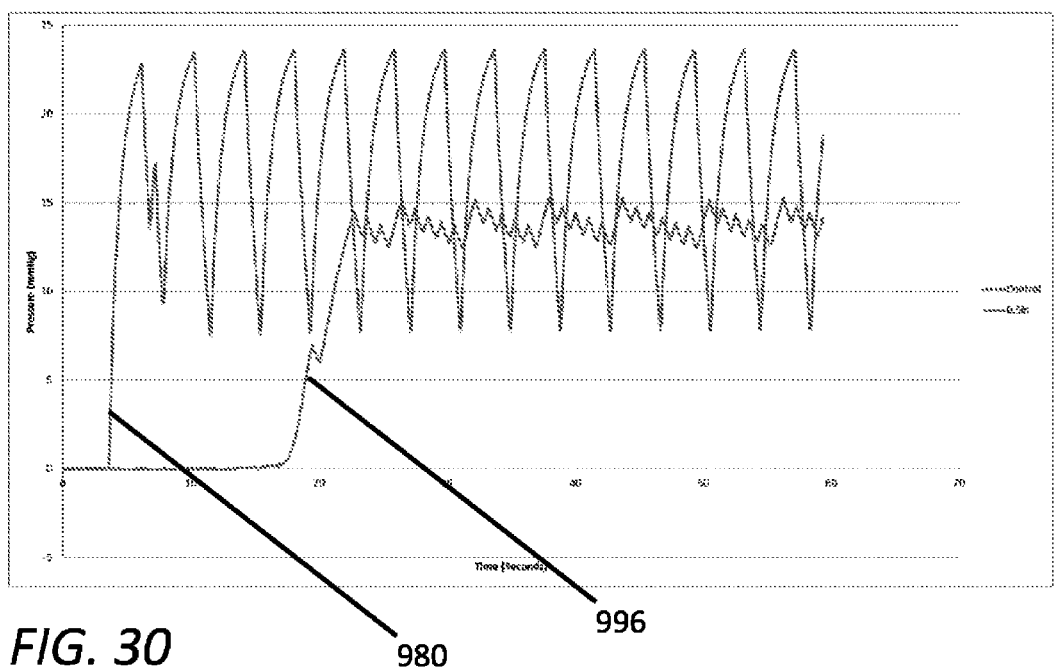
FIG. 30 is a graph of surgical site pressure over time for a simulated surgical access site insufflated with a pulsatile insufflation pump and another embodiment of pressure conditioning apparatus.

With reference to FIG. 28, a pressure plot 992 of a pressure conditioning apparatus having an outlet tubing with an inner diameter of 0.15 inches is illustrated in comparison to a baseline pressure plot 980. As illustrated, the pressure conditioning profile maintains a pressure of approximately 13 mmHg, with a pressure deviation of approximately 1 mmHg. With reference to FIG. 29, a pressure plot 994 of a pressure conditioning apparatus having an outlet tubing with an inner diameter of 0.25 inches is illustrated in comparison to a baseline pressure plot 980. As illustrated, the pressure conditioning profile maintains a pressure of approximately 14 mmHg, with a pressure deviation of approximately 1.5 mmHg. With reference to FIG. 30, a pressure plot 996 of a pressure conditioning apparatus having an outlet tubing with an inner diameter of 0.5 inches is illustrated in comparison to a baseline pressure plot 980. As illustrated, the pressure conditioning profile maintains a pressure of approximately 14.5 mmHg, with a pressure deviation of approximately 2 mmHg.

With continued reference to FIGS. 27-30, comparing the pressure conditioning profiles of various embodiments of pressure conditioning apparatus indicates that the smaller the outlet tubing inner diameter, the greater overall colorectal system pressure drop, but the smaller the pressure differential. Correspondingly, a relatively larger tubing inner diameter tends to yield a pressure conditioning profile with minimized colorectal system pressure drop and a relatively larger pressure differential.

It can be desirable that the insufflation pressure maintained by the surgical site access system has a relatively low pressure drop and a pressure deviation that is clinically acceptable. Accordingly, in some embodiments, the outlet tubing can have an inner diameter that is desirably in the range of from approximately 0.25 inches to approximately 0.5 inches. In certain embodiments, the outlet tubing can have an inner diameter of approximately 0.5 inches. Advantageously, a 0.5 in inner diameter tubing has a relatively small pressure drop and a clinically acceptable pressure differential. In a cadaver lab, a pressure differential of 2 mmHg was not visually noticeable. Therefore, the pressure differential caused a 0.5 in inner diameter tubing is acceptable. Insufflation tubing such as the inlet tubing coupling the pressure conditioning apparatus to an insufflation pump can typically have an inner diameter of approximately 0.25 inches. Thus, it is desirable that the outlet tubing has a larger inner diameter than the inlet tubing. In the embodiment of pressure conditioning apparatus having an outlet tube with a 0.5 inch inner diameter, the inner diameter of the outlet tubing can be at least twice the inner diameter of the inlet tubing.

In certain other embodiments, it is contemplated that a pressure conditioning apparatus can comprise other mechanical or electromechanical systems to condition pulsing flow from an insufflation pump to maintain substantially constant pressure at a surgical site despite leakage, absorption, and a pulsing input. In some embodiments, a source of compressed air, which may be available for use in a surgical workspace, can be used to condition a pulsing gas flow from an insufflation pump. With reference to FIG. 31, in some embodiments, a pressuring conditioning apparatus 1000 comprises an insufflation gas reservoir 1020 with a thin, gas impermeable membrane dividing the reservoir 1020 into an insufflation chamber 1024 and a pressurization chamber 1026. A compressed air source, such as a compressed air tank 1040 can provide air, regulated to a desired pressure by a pressure regulator 1042 to a pressure port 1044 of the pressurization chamber 1026. The pressurization chamber 1026 also includes a check valve 1028 to maintain a desired pressure within the insufflation chamber 1024 and pressurization chamber 1026.

With continued reference to FIG. 31, in operation, the insufflation pump 1010 is fluidly coupled to the insufflation chamber 1024 at an inlet port 1015 and fills the insufflation chamber 1024 to capacity with insufflation gas at a desired pressure. The compressed air tank 1040 then pressurizes the pressurization chamber 1026 of the reservoir 1022 to a pressure slightly below that desired for the system and lower than that required to open the check valve 1028. Reduced backpressure at an outlet port 1030 of the insufflation chamber 1024 due to gas leakage or absorption from the surgical site in the system will cause the pressure of the insufflation chamber 1024 to drop if the insufflator 1010 is not continuously pressurizing the system. When the insufflator turns off, pressurized air from the pressurization chamber 1026 of the reservoir 1020 acts on the flexible membrane 1022 to maintain pressure within the insufflation chamber 1024 and maintain a substantially continuous supply of insufflation gas to the patient.

Thus, advantageously, a pressurized two chamber reservoir can prevent a large pressure fluctuation at a surgical site despite discontinuities in insufflation gas flow and gas leakage and absorption at the surgical site. As the insufflation pump 1010 reengages to increase pressure in the system, the insufflation gas is pushed into the insufflation chamber 1024 of the reservoir 1020 causing the check valve 1028 to open as pressurized air is vented to return the pressurization chamber 1026 to a desired pressure. The cycle of pressurized gas addition to the pressurization chamber 1026 to maintain insufflation gas pressure in the insufflation chamber 1024 and pressurized gas venting through a check valve 1028 as the insufflation chamber 1024 is pressurized by the insufflation pump 1010 repeats as needed responsive to insufflation gas flow fluctuations and gas leakage and absorption at the surgical site.

With reference to FIG. 32, another embodiment of pressure conditioning apparatus 1100 is schematically illustrated. The apparatus receives a flow of insufflation gas from an insufflation pump 1110, the gas flow is monitored by a flow sensor 1112, as it passes through an inlet port 1115 to an insufflation chamber 1124 of a reservoir 1120. The gas flow exits the insufflation chamber 1124 at an outlet port 1130 fluidly coupled to a surgical site. Pressure conditioning can be supplied to the reservoir 1120 by a sliding piston or plunger 1122 coupled to a linear actuator 1140 with position feedback. A programmable logic controller 1160 can monitor position data from the linear actuator 1140, pressure data from a surgical site pressure sensor 1114, and gas flow data from the flow sensor 1112 to control the response of the system as a function of the inputs received from the sensors. Electrical coupling of the system components are illustrated by dashed lines in FIG. 32. The programmable logic controller 1160 can be electrically coupled to the sensors 1112, 1114 and linear actuator 1140 by a wired or wireless connection. A power supply 1150 is electrically coupled to the programmable logic controller 1160 to supply power thereto and can also provide power to the linear actuator 1140.

In use, in conjunction with the insufflation pump 1110 providing insufflation gas in a discontinuous or pulsed flow profile, the pressure conditioning apparatus 1100 can provide consistent pressurization of a system despite leakage and/or a pulsing gas flow. In operation, the insufflation pump 1110 fills the insufflation chamber 1124 of the reservoir 1112 to capacity with insufflation gas at the desired pressure. The flow sensor 1112 is able to detect when the insufflator is engaged in pressurizing the system and when it is not. Leakage and absorption in the system at the surgical site will cause the pressure to drop if the insufflation pump 1110 is not continuously pressurizing the system. When the insufflation pump 1110 disengages, the flow sensor 1112 detects the state of the insufflator and the plunger 1122 is driven forward by the linear actuator 1140 to maintain a pressure slightly lower than that desired while acquiring constant feedback from the pressure sensor 1114 at the surgical site. Keeping the pressure lower than desired will allow the insufflation pump 1110 to detect a leak in the system prior to the reservoir 1120 fully depleting while minimizing the fluctuation from insufflation pump 1110 state cycling. When the insufflation pump 1110 reengages to increase the pressure in the system, the flow sensor 1112 triggers the plunger 1122 to slowly recess, allowing the insufflation chamber 1124 of the reservoir 1120 to refill. The cycle of linear actuator advancement and retreating movement repeats as needed to maintain a substantially constant pressure at a surgical site.

Figure 33:
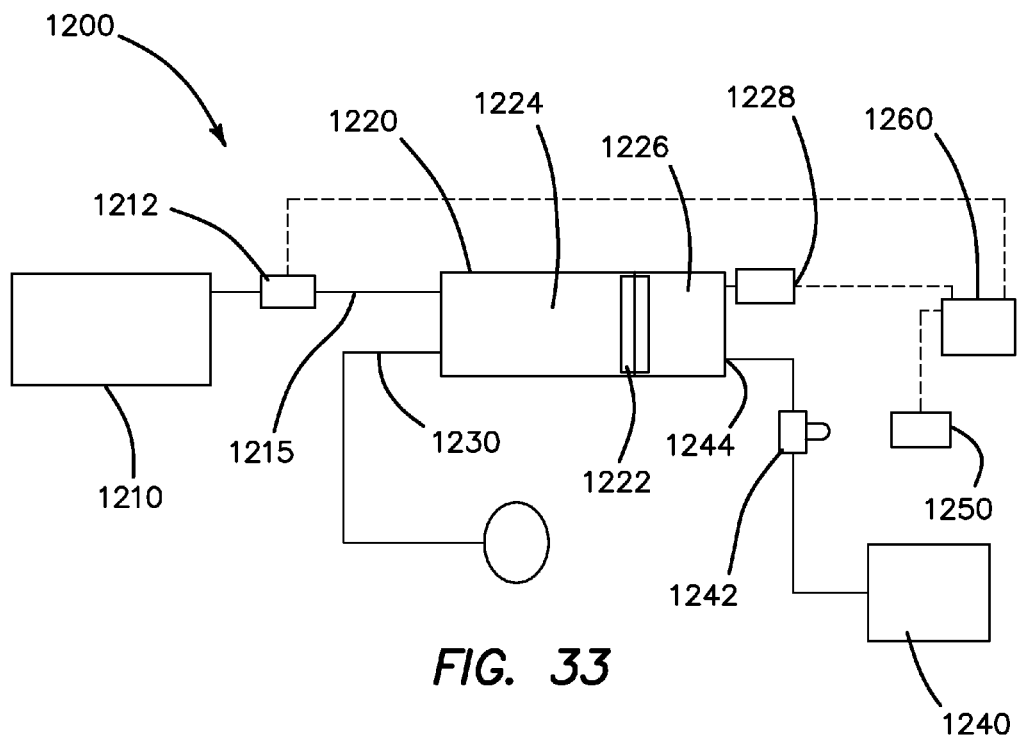
FIG. 33 is a schematic view of another embodiment of insufflation system.

With reference to FIG. 33, another embodiment of pressure conditioning apparatus 1200 is schematically illustrated. The pressure conditioning apparatus 1200 can comprise a reservoir 1220 having a free sliding piston 1222 disposed therein that divides the reservoir 1220 into an insufflation chamber 1224 and a pressurization chamber 1226. In other embodiments, another separation member such as a thin film membrane can divide the reservoir into insufflation and pressurization chambers, as described with respect to FIG. 31 above. An insufflation pump 1210 provides gas flow to an inlet port 1215 of the reservoir 1220 through a flow sensor 1212. The flow sensor 1212 is electrically coupled to a programmable logic controller 1260 by a wired or wireless connection. The pressurization chamber 1226 of the reservoir 1220 is supplied compressed air from a compressed air source such as a compressed air tank 1240 through a pressure regulator 1242. A solenoid valve 1228 that is electrically coupled to the programmable logic controller 1260 (PLC) can maintain a desired pressure in the pressurization chamber 1226 as a function of inputs received from the flow sensor 1212. The PLC 1260 can be powered by a power supply 1250 electrically coupled thereto. In other embodiments, a check valve can be used instead of the solenoid valve 1228, and the apparatus can operate substantially as described with respect to the embodiment of FIG. 31 without a PLC and flow sensor.

In conjunction with the insufflation pump, the pressure conditioning apparatus 1200 provides consistent pressurization of a system despite pulsing insufflation gas flow and leakage or absorption at a surgical site. In operation, the insufflation pump 1210 fills the insufflation chamber 1224 of the reservoir 1220 to capacity with insufflation gas at a desired pressure. The compressed air tank 1240 and pressure regulator 1242 then pressurize the pressurization chamber 1226 of the reservoir 1220 to a pressure slightly below that desired for the surgical site. The flow sensor 1212 is able to detect when the insufflation pump 1210 is engaged in pressurizing the system and when it is not. Leakage and absorption of insufflation gas from the surgical site will cause the pressure to drop by reducing backpressure at the outlet port 1230 of the insufflation chamber 1224 if the insufflation pump 1210 is not continuously pressurizing the apparatus 1200. When the insufflation pump 1210 is not providing a pressure pulse, the compressed air supplied from the compressed air tank 1240 to the pressurization chamber 1226 of the reservoir 1220 presses against the piston 1220, sliding the piston towards the insufflation chamber 1224 to maintain the supply of insufflation gas to the surgical site and prevent a large pressure fluctuation from the leak. As the insufflation pump 1210 reengages to increase pressure, the flow sensor 1212 triggers the PLC 1260 to open the solenoid valve 1228, allowing insufflation gas supplied to the insufflation chamber 1224 advance the piston 1222 towards the pressurization chamber 1226. The PLC can close the solenoid valve 1228 at a predetermined elapsed time, insufflation flow condition, or some other factor. The cycle of the piston sliding towards the insufflation chamber 1224 then towards the pressurization chamber 1226 repeats as needed responsive to variations in flow from the insufflation pump 1210 and leakage and absorption at the surgical site.

Figure 34A:
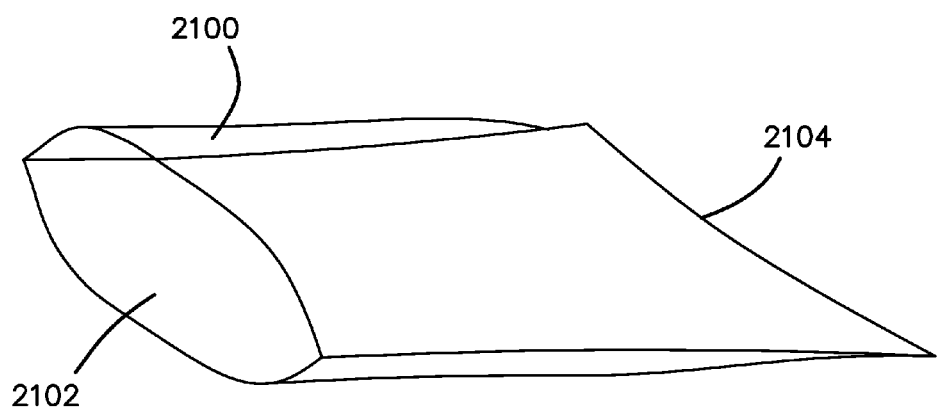
FIG. 34A is a perspective view of an embodiment of body conduit sealing device.
Figure 34B:
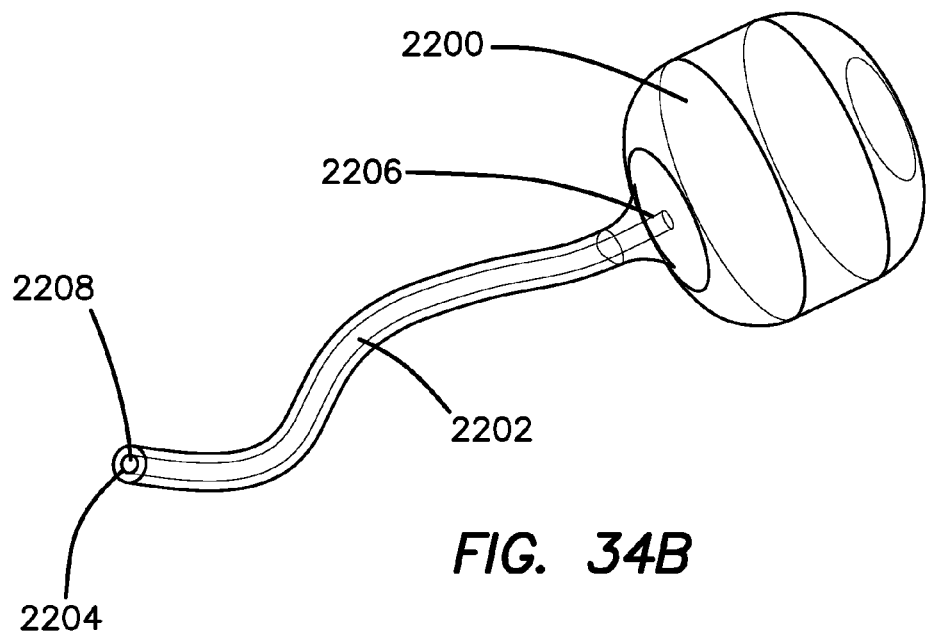
FIG. 34B is a perspective view of another embodiment of body conduit sealing device.
Figure 34C:
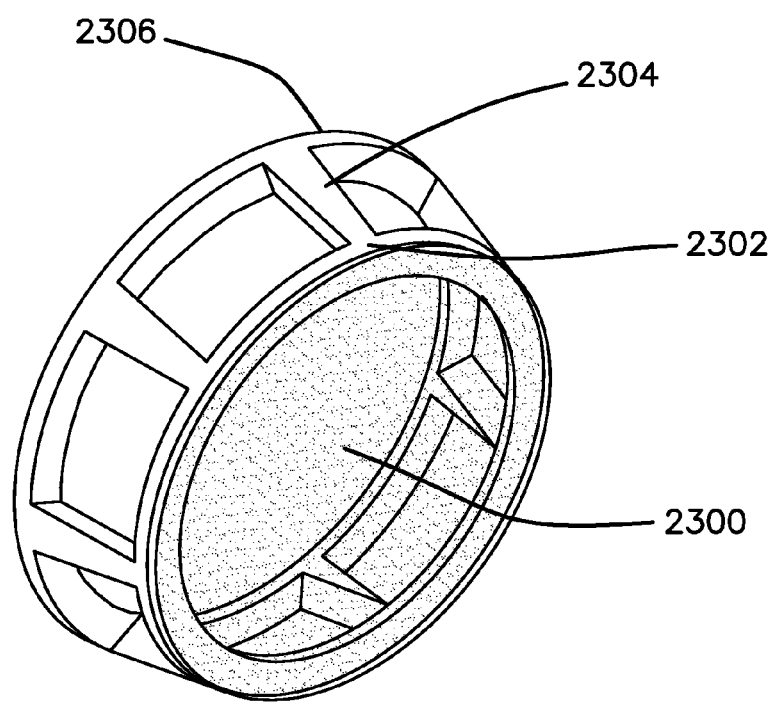
FIG. 34C is a perspective view of another embodiment of body conduit sealing device.

With reference to FIGS. 34A-34C, embodiments of surgical site sealing apparatus for sealing an open ended body conduit are illustrated. In some TAMIS procedures or other surgical procedures involving insufflation of an open-ended body conduit, a sealing apparatus can be positioned to form a closed, inflatable compartment within the open-ended conduit. Thus, leakage of insufflation gas from an open end of the conduit can be minimized. Various embodiments of sealing apparatus can be used to minimize billowing of the body conduit in an insufflation system in conjunction with a pressure conditioning apparatus as described herein. The sealing apparatuses can also reduce billowing of the body conduit when used with an unconditioned pulsing insufflation pump as gas leakage from an open end of the conduit can be reduced.

With reference to FIG. 34A, a surgical site sealing apparatus can comprise an elastomeric bag 2100 having an open end 2102 and a closed end 2104 opposite the open end 2102. The elastomeric bag 2100 can be sized and configured to be positioned within a body conduit such the rectum for a TAMIS procedure. The elastomeric bag 2100 can be inflatable such that it has an insertion configuration in which the bag 2100 is advanceable within the body conduit in an undisturbed state. The elastomeric bag 2100 can then be inflated to an insufflated condition in which the elastomeric bag distends the body conduit. Insufflation gas such as $CO_2$ is retained within the elastomeric bag 2100 in the body conduit, such as a rectal cavity. Accordingly insufflation pressure losses due to leakage from a body conduit at a surgical site and absorption can be minimized. A surgeon can remove a section of the elastomeric bag 2100 to access a wall of the body conduit for surgical treatment.

With reference to FIG. 34B another embodiment of surgical site sealing apparatus for sealing an open ended body conduit is illustrated. As illustrated, the sealing apparatus can comprise an inflatable member such as a balloon 2200 or pouch that is fluidly coupled to an inflation fluid supply tube 2202. The inflatable member can have a deflated state in which it is sized to be advanced through an open end of a body conduit. Once positioned at a desired location in the body conduit, the inflatable member is inflatable by fluid to an inflated state sized to sealingly engage with walls of the body conduit.

The inflation tube 2202 extends from a proximal end 2204 to a distal end 2206 and having a lumen 2208 extending between the proximal end 2204 and the distal end 2206. The distal end 2206 of the inflation tube 2202 is coupled to the inflatable member. The lumen 2208 is fluidly coupled to the inflatable member to provide the fluid to the inflatable member. The inflation tube 2202 can have a length sufficient to maintain the proximal end 2204 proximal an open end of the body conduit.

In use, the balloon 2200 in the deflated state can be advanced to a position in a body conduit beyond a desired treatment site, then inflated to sealingly engage with walls of the body conduit and create a closed volume in the body conduit that includes the treatment site. A surgical procedure can then be performed at the treatment site. Once the surgical procedure has been performed, the balloon can be deflated and inflation tube 2202 can be removed from the body conduit by pulling the inflation tube 2202. Thus, the inflation tube 2202 can additionally function as a tether to facilitate removal of the balloon 2200.

With reference to FIG. 34C another embodiment of surgical site sealing apparatus for sealing an open ended body conduit is illustrated. As illustrated, the sealing apparatus can comprise a flexible diaphragm 2300. The sealing apparatus can further comprise a flexible ring 2302 disposed around the diaphragm. The flexible ring 2302 can be configurable, such as by compressing it, bending, twisting, or rolling, in a first configuration in which the flexible ring 2302 is advanceable through the body conduit beyond a treatment site. Once positioned beyond the treatment site, the bend, twist, or roll of the flexible ring 2302 is released, and a bias of the ring 2302 tends to configure the ring in a second configuration in which the flexible ring 2302 is generally circular such that it is sealingly engageable with a wall of the body conduit. In the illustrated embodiment, the flexible ring 2302 can further comprise a second, outer ring 2306 coupled to the flexible ring 2302 by a plurality of ribs 2304. This double-ring construction can enhance sealing engagement of the ring with a body conduit having surface irregularities.

With the ring sealingly engaging the wall of the body conduit, a closed volume of the body conduit has been created. Thus a surgical treatment procedure can be performed at a treatment site within the closed volume. Following the surgical treatment procedure, the sealing apparatus can be removed.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A gas flow pressure conditioning apparatus for use with a pulsing insufflation pump, the apparatus comprising:
    an inlet fluid port configured to receive a flow of gas from the pulsing insufflation pump;
    an outlet fluid conduit configured to provide a flow of insufflation gas to a surgical site;
    a reservoir fluidly coupled to the inlet fluid port and the outlet fluid conduit, the reservoir comprising an elastomeric pouch formed of a film material configured to expand and contract responsive to the flow of gas at the inlet fluid port and the flow of insufflation gas at the outlet fluid conduit; and
    wherein the inlet fluid port has a first inner diameter and the outlet fluid conduit has a second inner diameter larger than the first inner diameter.

2. The gas flow pressure conditioning apparatus of claim 1, further comprising an inlet fluid conduit fluidly coupled to the inlet fluid port.

3. The gas flow pressure conditioning apparatus of claim 1, wherein the elastomeric pouch comprises an outlet port fluidly coupled to the outlet fluid conduit.

4. The gas flow pressure conditioning apparatus of claim 1, wherein the elastomeric pouch has a volume of at least about 6.5 liters.

5. The gas flow pressure conditioning apparatus of claim 1, wherein the second inner diameter is at least twice the first inner diameter.

6. The gas flow pressure conditioning apparatus of claim 1, further comprising an outer envelope positioned around the reservoir.

7. The gas flow pressure conditioning apparatus of claim 6, wherein the outer envelope comprises an elastomeric film material.

8. The gas flow pressure conditioning apparatus of claim 1, further comprising an outer sleeve positioned around the reservoir.

9. The gas flow pressure conditioning apparatus of claim 8, wherein the outer sleeve is heat welded to the reservoir at a seam.

10. An insufflation system comprising:
 a surgical site access port comprising:
  a port surface;
  an access port insufflation port having a first insufflation diameter;
  a first trocar positionable through the port surface, the first trocar having a first instrument channel extending therethrough; and
  a second trocar positionable through the port surface, the second trocar having a second instrument channel extending therethrough and a trocar insufflation port having a second insufflation diameter greater than the first insufflation diameter of the access port insufflation port; and
 a gas flow pressure conditioning apparatus for use with a pulsing insufflation pump, the apparatus comprising:
  an inlet fluid conduit configured to receive a flow of gas from the pulsing insufflation pump;
  an outlet fluid conduit configured to provide a flow of insufflation gas to the surgical site access port; and
  a reservoir fluidly coupled to the inlet fluid conduit and the outlet fluid conduit; and
 wherein the inlet fluid conduit has a first inner diameter and the outlet fluid conduit has a second inner diameter larger than the first inner diameter.

11. The insufflation system of claim 10, wherein the trocar insufflation port of the second trocar is sized to receive the outlet fluid conduit.

12. The insufflation system of claim 10, wherein the reservoir comprises an elastomeric film pouch.

13. The insufflation system of claim 10, wherein the reservoir has a volume of at least 6.5 liters.

14. The insufflation system of claim 10, wherein the second inner diameter is greater than at least about 0.25 inches.

15. The insufflation system of claim 10, wherein the second inner diameter is approximately 0.5 inches.

* * * * *